(12) United States Patent
El Katerji et al.

(10) Patent No.: US 12,390,168 B2
(45) Date of Patent: *Aug. 19, 2025

(54) SYSTEMS AND METHODS FOR ESTIMATING A POSITION OF A HEART PUMP

(71) Applicant: ABIOMED, Inc., Danvers, MA (US)

(72) Inventors: Ahmad El Katerji, Danvers, MA (US); Chen Liu, Danvers, MA (US)

(73) Assignee: ABIOMED, Inc., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/539,929

(22) Filed: Dec. 14, 2023

(65) Prior Publication Data

US 2024/0260905 A1 Aug. 8, 2024

Related U.S. Application Data

(60) Continuation of application No. 17/686,560, filed on Mar. 4, 2022, now Pat. No. 11,883,207, which is a
(Continued)

(51) Int. Cl.
*A61M 60/531* (2021.01)
*A61B 5/00* (2006.01)
(Continued)

(52) U.S. Cl.
CPC .......... *A61B 5/7239* (2013.01); *A61M 60/13* (2021.01); *A61M 60/148* (2021.01);
(Continued)

(58) Field of Classification Search
None
See application file for complete search history.

(56) References Cited

U.S. PATENT DOCUMENTS

| 4,128,325 A | 12/1978 | Melander et al. |
| 5,964,694 A | 10/1999 | Siess et al. |

(Continued)

FOREIGN PATENT DOCUMENTS

| CN | 1222863 A | 7/1999 |
| CN | 106573093 A | 4/2017 |

(Continued)

OTHER PUBLICATIONS

Office Action from corresponding European Patent Application No. 19714058.5 dated Feb. 9, 2024 (5 pp.).
(Continued)

*Primary Examiner* — Erica S Lee
(74) *Attorney, Agent, or Firm* — BOTOS CHURCHILL IP LAW LLP

(57) ABSTRACT

Systems and methods are provided herein for estimating a position of a heart pump system in a patient. The system receives first data indicative of a time-varying motor current during a first time period. The motor current corresponds to an amount of current delivered to a motor, while the heart pump system is operating in the patient. The system receives second data indicative of a time-varying differential pressure during the first time period. The differential pressure is indicative of a position of the heart pump system relative to patient's heart. The system receives third data indicative of time-varying motor current during a second time period, and determines an estimate of differential pressure during the second period of time from the third data and a relationship between the first data and the second data. The estimate is usable to predict the position of the heart pump system in the patient.

19 Claims, 18 Drawing Sheets

Related U.S. Application Data division of application No. 16/354,595, filed on Mar. 15, 2019, now Pat. No. 11,298,524.

(60) Provisional application No. 62/644,240, filed on Mar. 16, 2018.

(51) Int. Cl.

| | | |
|---|---|---|
| *A61M 60/13* | (2021.01) | |
| *A61M 60/148* | (2021.01) | |
| *A61M 60/174* | (2021.01) | |
| *A61M 60/216* | (2021.01) | |
| *A61M 60/411* | (2021.01) | |
| *A61M 60/538* | (2021.01) | |
| *A61M 60/554* | (2021.01) | |
| *A61M 60/816* | (2021.01) | |
| *A61M 60/829* | (2021.01) | |
| *A61M 60/867* | (2021.01) | |
| *A61B 5/024* | (2006.01) | |

(52) U.S. Cl.
CPC ........ *A61M 60/174* (2021.01); *A61M 60/216* (2021.01); *A61M 60/411* (2021.01); *A61M 60/538* (2021.01); *A61M 60/554* (2021.01); *A61M 60/816* (2021.01); *A61M 60/829* (2021.01); *A61M 60/867* (2021.01); *A61B 5/0031* (2013.01); *A61B 5/024* (2013.01); *A61M 2205/3331* (2013.01); *A61M 2205/3334* (2013.01); *A61M 2205/3344* (2013.01); *A61M 2205/3351* (2013.01); *A61M 2205/3355* (2013.01)

(56) References Cited

U.S. PATENT DOCUMENTS

| | | | |
|---|---|---|---|
| 6,176,822 B1 * | 1/2001 | Nix .................... | A61M 60/816 623/3.1 |
| 7,022,100 B1 | 4/2006 | Aboul-Hosn et al. | |
| 2003/0045772 A1 * | 3/2003 | Reich .................. | A61M 60/216 600/18 |
| 2004/0022640 A1 | 2/2004 | Siess et al. | |
| 2015/0141842 A1 | 5/2015 | Spanier et al. | |
| 2015/0290372 A1 | 10/2015 | Muller et al. | |
| 2017/0035952 A1 | 2/2017 | Muller | |
| 2017/0182232 A1 * | 6/2017 | Rudser ................ | A61M 60/515 |
| 2017/0292501 A1 * | 10/2017 | Perley .................... | F03D 17/00 |
| 2018/0055979 A1 | 3/2018 | Corbett et al. | |
| 2018/0064860 A1 | 3/2018 | Nunez et al. | |
| 2018/0078159 A1 * | 3/2018 | Edelman .............. | A61B 5/4848 |
| 2018/0279896 A1 | 10/2018 | Ruppersberg | |

FOREIGN PATENT DOCUMENTS

| | | |
|---|---|---|
| EP | 3515523 A1 | 7/2019 |
| JP | 2000512191 A | 9/2000 |

OTHER PUBLICATIONS

Examination report for corresponding IN Application No. 202017043847 dated Jul. 27, 2022, (6 pp.).
International Search Report and Written Opinion in International Application No. PCT/US2019/022535 dated Jun. 14, 2019 (14 pp.).
Office Action from corresponding Chinese Patent Application No. 201980032393.5 dated Jun. 1, 2023 (21 pp.).
Office Action from corresponding Israeli patent application No. 277736 dated Jul. 4, 2023 (4 pp.).
Office Action from corresponding Japanese Patent Application No. 2020-549647 dated Mar. 30, 2023 (14 pp.).
Office Action from corresponding Korean Patent Application No. 10-2020-7029861 dated Jan. 8, 2024 (19 pp.).
Office Action dated Oct. 31, 2024 for IL Patent Application No. 313884 (4 pp.).
Office Action from corresponding Australian Patent Application No. 2019236250 dated Oct. 17, 2024 (3 pp.).

\* cited by examiner

SYSTEMS AND METHODS FOR ESTIMATING A POSITION OF A HEART PUMP

CROSS-REFERENCE TO RELATED APPLICATIONS

This application is a continuation of U.S. patent application Ser. No. 17/686,560, filed Mar. 4, 2022, now U.S. Pat. No. 11,883,207, which is a divisional of U.S. patent application Ser. No. 16/354,595, filed Mar. 15, 2019, now U.S. Pat. No. 11,298,524, which claims the benefit of U.S. Provisional Patent Application No. 62/644,240, filed Mar. 16, 2018, and is related to International Application No. PCT/US2019/022535, filed Mar. 15, 2019, the disclosures of all of which are hereby incorporated by reference in their entirety.

BACKGROUND OF THE INVENTION

Acute and chronic cardiovascular conditions reduce quality of life and life expectancy. A variety of treatment modalities have been developed for heart health, ranging from pharmaceuticals to mechanical devices and transplantation. Temporary cardiac support devices, such as heart pump systems, provide hemodynamic support, and facilitate heart recovery. Some heart pump systems are percutaneously inserted into the heart and can run in parallel with the native heart to supplement cardiac output, such as the IMPELLA® family of devices (Abiomed, Inc., Danvers MA). Such heart pump systems may measure and/or calculate heart pump parameters useful for determining patient health and judging operation of the heart pump system.

These measurements may be collected through sensors, which are prone to failure. When heart pump system sensors fail, clinicians lose many valuable measurements, such as flow estimation, position monitoring, and suction alarms. If sensors fail, clinicians often remove the heart pump system from the patient, even if the pump itself is functioning correctly. Removing and replacing the heart pump system, especially if the pump is functioning properly, is undesirable because doing so increases the risk of introducing bacteria to the patient. Replacing the heart pump system can be expensive and lead to a "wasted" heart pump system. Furthermore, removing and replacing the heart pump system may take away valuable time from the patient's blood pump support and therefore recovery.

BRIEF SUMMARY OF THE INVENTION

The systems, devices, and methods described herein provide an estimate of a position of a heart pump when positioned within a patient's heart. In particular, the systems and methods determine a relationship between motor current and a differential pressure signal for a specific heart pump system, and then use this relationship to determine an estimate of time-varying differential pressure from later-received motor current data. From the estimated differential pressure, the heart pump system estimates the pump flow, trigger suction alarms and trigger positioning alarms.

A controller may be configured to perform any of the implementations, aspects, and methods described herein. For example, the controller may be the Automated Impella Controller (AIC) of Abiomed, Inc or any other suitable controller. In some implementations, the heart pump system comprises a catheter; a motor; a rotor operatively coupled to the motor; a pump housing at least partially surrounding the rotor so that the actuating motor drives the rotor and pumps blood through the pump housing; one or more sensors, including a differential pressure sensor; and the controller. For example, the heart pump system may comprise the Impella RP heart pump or the Impella 5.0 heart pump of Abiomed, Inc connected to an AIC or any other suitable system.

The heart pump system may comprise a pump with a pump housing and a rotor. The rotor is at least partially positioned within the pump housing such that a motor drives the rotor and the rotor pumps blood through the pump housing while the system is operating. The heart pump system includes a cannula with a proximal end that interfaces with the distal end of the pump housing and a distal end. The pump may be configured to be placed such that cannula extends across an aortic valve of the patient, the distal end being located within a left ventricle of the patient, and the proximal end being located within an aorta of the patient. In some implementations, an elongate catheter extends proximal of the pump housing. The elongate catheter may be coupled on its distal end to the pump housing. In an example, a drive cable may extend through the elongate catheter. In an example, the elongate catheter may house electrical connections, connecting the pump to a controller. In some implementations, the pump further includes a flexible projection extending distally away from the distal end of the cannula, such as a pigtail-shaped flexible projection.

The heart pump system comprises one or more sensors that measure pressure, such as a differential pressure sensor. In an example, the differential pressure sensor measures the difference between the pressure outside the pump and the pressure inside the pump. For example, when the cannula is placed across the aortic valve, a top (outer surface) of the sensor is exposed to the aortic pressure and a bottom (inner surface) of the sensor is exposed to the ventricular pressure.

A controller operatively connected to the heart pump system estimates the position of the heart pump based on baseline data and updated data. The baseline data is received during a first period of time, and provides a basis for the controller to determine a relationship between two parameters during normal operation of the pump. The first period of time may be 20 seconds, 40 seconds, one minute, two minutes, ten minutes, twenty minutes or any other suitable period of time. The first period of time may correspond to a number of samples acquired at a given frequency. For example, the first period of time may correspond to 500 samples, 1000 samples, 2000 samples, 5000 samples, or any other suitable number of samples. Generally, during the first period of time, the heart pump system operates within a patient's body and sensors on-board and/or off-board the heart pump system acquire data related to the system operation (e.g., motor current, pump location, or any other motor or system parameter) and/or patient health (e.g., aortic pressure, differential pressure, or any other hemodynamic or patient parameter). This data is used to identify relationships between certain parameters. In the event of failure of one or more sensors (e.g., differential pressure), the controller may estimate a signal from the defective sensor(s) based on a working sensor (e.g., motor current) and the relationship between the signals from the failed sensor and the working sensor. During the first period of time, the pump may operate at a single performance level (e.g., correlating to a particular rotor speed) or a range of performance levels.

The controller receives first data indicative of a time-varying motor current in the heart pump system during the first period of time and receives second data indicative of a time-varying differential pressure for a patient during the first period of time. The time-varying motor current corresponds to an amount of current delivered to a motor of the heart pump system while the heart pump system is operating in the patient. For example, the motor current may change to keep a rotor speed of the heart pump system constant. Operating the motor (e.g., contained in motor housing 102 of FIG. 1) of the heart pump system to maintain a constant rotor speed, as is desirable in many medical situations, generally requires supplying the motor with varying amounts of current because the load on the motor varies during the different stages of the cardiac cycle of the heart. Accordingly, when the differential pressure in a patient's heart changes, the motor current also changes to keep the rotor speed constant. For example, when the flow rate of blood into the aorta increases (e.g., during systole), the current required to operate the motor increases. This increase in motor current can be used to characterize cardiac function as is discussed further below. The time-varying differential pressure corresponds to a difference in pressure between an inner portion of the heart pump system and an outside of the heart pump system and is further indicative of a position of the heart pump system relative to a patient's heart. The differential pressure signal is indicative of pressure over time, and the measurements displayed may be derived from a pressure sensor on the intravascular pump during operation of the pump. For example, the sensor may detect an electrical signal (also referred to as a differential pressure signal), which is proportional to the difference between aortic pressure and ventricular pressure, and which may be displayed by the heart pump system. As described below, the systems and methods described herein determine a relationship between the time-varying motor current and the time-varying differential pressure. The relationship between motor current and differential pressure may be used in conjunction with motor current data to estimate differential pressure at other points in time (e.g., after the first period of time, described above). This is particularly useful if the pressure sensor fails, or if it is desirable to confirm operation of the pressure sensor.

During a second period of time later than the first period of time, the controller receives third data indicative of time-varying motor current. For example, the second period of time may be 1 second, 2 second, 10 seconds, 30 seconds, 1 minute, 2 minutes, 10 minutes, or any suitable length of time. For example, the controller receives data relating to time-varying motor current and differential pressure at a first time, and then later receives additional motor current data during the second period of time. The data from the first period of time may be used to determine a relationship between the first data (indicative of motor current during the first time period) and the second data (indicative of differential pressure during the first time period).

The controller determines an estimate of time-varying differential pressure during the second period of time from the third data and a relationship between the first data (indicative of motor current during the first time period) and the second data (indicative of differential pressure during the first time period). For example, the relationship between the first data and the second data may be multilinear fit of a mapping between the motor current and the differential pressure information acquired during the first time period. The relationship between motor current and differential pressure may be characteristic of a given heart pump system—i.e., at a particular performance level, the relationship between the motor current and differential may be substantially similar at different points in time and the relationship itself may be "scalable" between different performance levels. Thus, determining the relationship between motor current and differential pressure during a first period of time may allow the systems and methods described herein to characterize the heart pump system and use the relationship at later points in time and at different performance levels.

The estimate of differential pressure is usable to predict the position of the heart pump system in the patient. For example, the controller may use the relationship between the motor current and differential pressure in conjunction with the more recently acquired third data (indicative of motor current during the second time period) to build an estimated differential pressure signal for the second time period. The controller may use the estimated differential pressure signal to determine the position of the heart pump system within the patient.

In some implementations, the systems, methods, and devices described herein determine a correlation between the motor current and the time-varying differential pressure for each point in time. In some implementations, the controller may compute multilinear fit of the correlation. The multilinear fit is indicative of operating characteristics of the heart pump system. For example, at each measured value of motor current at each point in time in the first time period a respective differential pressure measurement at the same point in time may be plotted. This plot may be used to determine a multilinear fit represented by a function or series of functions, which may differ between individual heart pump systems. For example, a first heart pump system may have a multilinear fit entirely different from a second heart pump system. As described below, the correlation between motor current and time-varying differential pressure may be scaled (linearly or using any appropriate scale) between differential performance levels for the same heart pump system. After the controller determines the correlation between the motor current and differential pressure, that correlation can be later used to characterize parameters of patient health and system operation. This is particularly useful in the event of sensor (e.g., pressure sensor) failure because the correlation may be used to estimate parameters that can no longer be directly measured from the sensor.

In some implementations, the second data (indicative of time-varying differential pressure) is received from a differential pressure sensor on the heart pump system. For example, when the heart pump system is placed within the patient's heart in an operating position, one side or surface of the differential pressure sensor may be exposed to the aortic pressure, a second side or surface of the differential pressure sensor may be exposed to the ventricular pressure, and the differential pressure sensor may measure the difference between the aortic and ventricular pressures. The placement and sensor type of the pressure sensor is not limiting. For example, the second data may be collated from multiple sensors on-board or off-board the heart pump system.

The differential pressure sensor may fail or break. In some implementations, if the differential pressure sensor fails, the controller determines the estimate of time-varying differential pressure during the second period of time in response to a determination of the sensor failure. In some implementations, the controller may determine that the differential pressure sensor has failed if no data is received from the differential pressure sensor during the second period of time. If the pressure sensor fails or breaks, the controller may no longer receive data directly relating to pressure in the patient's heart. For a system in which the placement of the heart pump system in the patient heart is determined from the pressure signal, a failure or break of the pressure sensor means that it is difficult or impossible to tell if the heart pump system is positioned properly within the patient's heart (e.g., extending across the aortic valve into the left ventricle). Accordingly, rather than directly measuring the differential pressure, the differential pressure is estimated, and the estimated values are used to determine placement of the heart pump system.

In some implementations, the systems, methods, and devices described herein determine the estimate of time-varying differential pressure during the second period of time comprises determining a time series of estimated points by determining whether the third data corresponds to a first phase or a second phase in the relationship between the first data and the second data. For example, the first phase may be Phase A and the second phase may be Phase B. For a given motor current value, there may be two corresponding differential pressure values, as determined by the relationship between the first data and the second data (e.g., as shown in FIG. 3). Of the two corresponding differential pressure values, one value may correspond to Phase A, while the other corresponds to Phase B.

Whether the motor current is in the first phase (e.g., Phase A) or the second phase (e.g., Phase B) may be determined by examining a diastolic period. In some implementations, the systems, methods, and devices described herein determine a diastolic period within the additional data (e.g., during the second time period described above). The diastolic period starts at a starting point and ends at an ending point in time. A slope of the additional data between the starting point and the ending point is indicative of the first phase or the second phase. If the slope is positive, the additional data corresponds to the first phase. If the slope is negative, the additional data corresponds to the second phase. Thus, by examining the diastolic period of a patient's heart, the systems and methods described herein may appropriately determine which of two pressure values (Phase A or Phase B) is correct for a given motor current value.

In some implementations, the systems, methods, and devices described herein determine, based on the estimate of time-varying differential pressure, at least one of: flow rate, position, and suction associated with the heart pump system. The time-varying differential pressure, the motor current, and/or the estimate of time-varying differential pressure may be displayed. In an example, the controller may display the time-varying differential pressure, the motor current, and the estimate of time-varying differential pressure simultaneously. In an example, the controller may display the motor current, and simultaneously display one of the time-varying differential pressure or the estimate of time-varying differential pressure. In an example, a user may select which signals he or she would like to view. Because determinations such as flow rate, position, and suction are based on differential pressure measurements or estimations, it is imperative the differential pressure value be known and correct for a given time. If the differential pressure sensor on a heart pump system fails, and no estimate for the pressure is determined, the flow rate, position, and suction of the system will also fail. By providing a differential pressure estimate, the systems and methods described herein thus also allow for continued flow rate, position, and suction estimations in the event of sensor failure, providing clinicians with a clearer picture of patient health and heart pump operation.

In some implementations, the systems, methods, and devices described herein provide first and/or second indicators relating to differential pressure sensor failure and the estimated time-varying differential pressure. The first indicator indicates that the differential pressure sensor has failed. In an example, the controller may display a warning indicator that says the sensor data is unreliable on a user interface. The second indicator indicates that the estimate of time-varying differential pressure during the second period of time is simulated or estimated. In an example, the controller may simultaneously display an alarm warning that the differential pressure sensor has failed and an alarm warning that the estimate of time-varying differential pressure is displayed and is an estimate. The indicators may be visual or auditory.

In some implementations, the systems, methods, and devices described herein determine whether the time-varying differential pressure is drifting by comparing the time-varying differential pressure to the estimate of time-varying differential pressure for a second period of time. Based on comparing the time-varying differential pressure to the estimate of time-varying differential pressure, a difference between the time-varying differential pressure and the estimate of time-varying differential pressure over the second period of time is calculated. For example, the controller may display both the time-varying differential pressure and the estimate of time-varying differential pressure, and may calculate the difference between these two signals at a plurality of points of time during the second period of time. The difference is compared to a differential pressure signal threshold. The differential pressure signal threshold may be 10 mmHg, 15 mmHg, 20 mmHg, 40 mmHg, 60 mmHg, 80 mmHg, or any suitable amount. If the difference is greater than the differential pressure signal threshold, the time-varying differential pressure is drifting. For example, at a first point in time the difference between the time-varying differential pressure and the estimate of time-varying differential pressure may be 2 mmHg. At a second point in time after the first point in time, the difference may be 5 mmHg. At a third point in time after the second point in time, the difference may be 27 mmHg. In this example, the differential pressure signal threshold may be 25 mmHg, in which case the controller would determine the time-varying differential pressure is drifting at the third point in time. By determining whether the differential pressure signal is drifting, the systems and methods described herein provide a check for the correct operation of the sensor. For example, if the sensor is degrading, the pressure signal may drift and provide incorrect measurements to a clinician. The clinician may be notified of such drift if the estimated differential pressure and the measured differential pressure differ significantly, giving the clinician an opportunity to correct or further examine pressure readings.

In some implementations, if the time-varying differential pressure is drifting, the systems, methods, and devices described herein display a notice indicating the differential pressure sensor needs to be re-calibrated. The notice may be visual or auditory. In an example, the controller may display a warning or alarm on a user interface stating that the time-varying differential pressure signal is unreliable and needs to be re-calibrated. In an example, the controller may display a warning or alarm on a user interface stating that the time-varying differential pressure signal is drifting. In some implementations, if the time-varying differential pressure is drifting, differential pressure sensor is automatically re-calibrated. In an example, the controller may zero the differential pressure sensor to re-calibrate. Re-calibration may help to ensure the sensor is providing accurate data to a clinician or controller, thereby increasing treatment efficacy.

In some implementations, the systems, methods, and devices described herein change operation of the heart pump system from a first operating level to a second operating level. Based on changing the operation of the heart pump system to the second level, the relationship between the first and second data may be scaled to account for the second operating level. The estimate of time-varying differential pressure may be based on scaling the relationship. In an example, during the first period of time, the heart pump system may be operating at operating level P-8, but during the second period of time the heart pump system may be operating at operating level P-9. The controller may determine the relationship between the relationship between the first and second data for operating level P-8. During the second period of time, the controller may calculate the estimate of the time-varying differential pressure by using the relationship calculated for the first time period to determine a value or set of values and then then linearly scaling that value or set of values. Thus, if the P-level used for collection of the motor current data and differential pressure signal data during the first time period is different from that used for collection of the additional motor current data during the second time period, the relationship between motor current and differential pressure sensor data may be scaled to account for the change in P-level.

DETAILED DESCRIPTION

Figure 1:
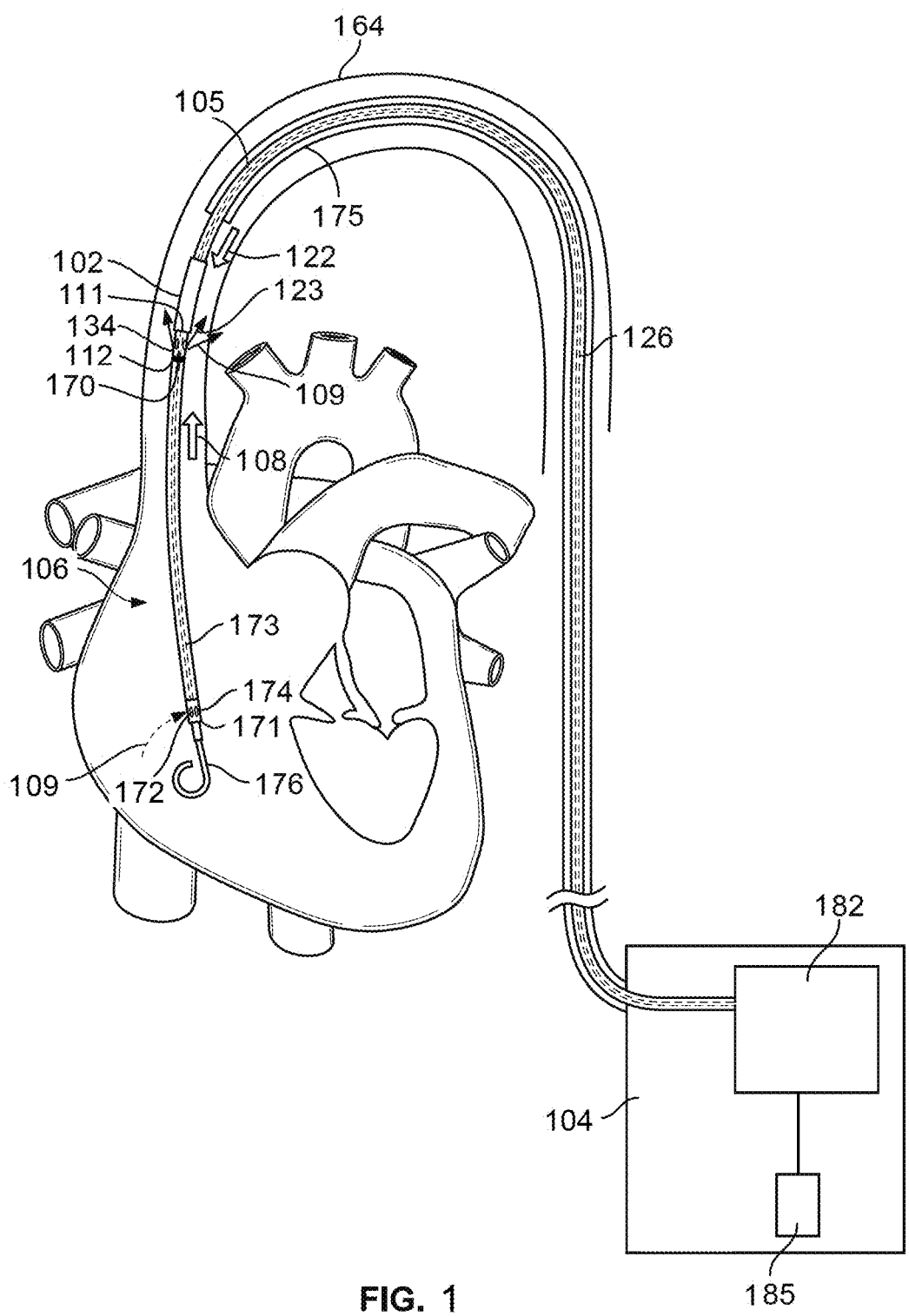
FIG. 1 shows an illustrative heart pump system configured to estimate cardiovascular parameters, according to certain implementations.

To provide an overall understanding of the systems, methods, and devices described herein, certain illustrative aspects will be described. Although the aspects and features described herein are specifically described for use in connection with patient heart health, it will be understood that all the components and other features outlined below may be combined with one another in any suitable manner and may be adapted and applied to other types of medical therapy and patient health.

The systems, devices, and methods described herein determine an estimate of time-varying differential pressure from motor current data using a relationship between past motor current and data and differential pressure data in a heart pump system. The differential pressure signal is indicative of pressure over time, and the measurements displayed may be derived from a pressure sensor on the intravascular pump (such as heart pump 100 in FIG. 1) during operation of the pump. For example, the sensor may detect an electrical signal (also referred to as a differential pressure signal), which is proportional to the difference between the pressure outside the pump and the pressure inside the pump, and which may be displayed by the heart pump system.

The differential pressure signal may be used by a clinician to determine the positioning of the pump within the heart by monitoring the measured pressure to determine when the pump is in a correct placement within the heart. When the heart pump is placed in the correct position across the aortic valve, the top (outer surface) of the sensor is exposed to the aortic pressure and the bottom (inner surface) of the sensor is exposed to the ventricular pressure. The heart pump system may be considered to be positioned properly when a cannula of the heart pump spans across the aortic valve such that a blood inlet to the pump is within the left ventricle and an outlet from the pump is within the aorta. When the heart pump system is properly positioned within the heart, changes in pressure associated with a cardiac cycle result in a pulsatile differential pressure signal. During diastole, the large pressure difference between the aorta and the left ventricle creates a large differential pressure signal. At the peak of systole, when the aortic valve opens, the pressure difference between the aorta and the left ventricle (and thus the differential pressure signal) is zero. Thus, the continual pressure changes associated with the cardiac cycle produce a pulsatile waveform when correctly positioned. When the heart pump system is not properly placed across the aortic valve, or when it is fully in the aorta or fully in the ventricle, the pressures outside and inside the cannula are the same throughout the cardiac cycle. As a result, the pressure on either side of the sensor membrane is the same, resulting in a flat differential pressure signal. For example, when correctly placed, the differential pressure signal may vary periodically and/or have peak-to-trough values of 60 mmHg, 40 mmHg, or another generally high value. When incorrectly placed, the differential pressure signal may have peak-to-trough values of 0 mmHg, 2 mmHg, or another generally low value.

The motor current signal is indicative of a measurement of the electrical current drawn by a motor in the heart pump system over time. The heart pump system (e.g., heart pump system 100) may be designed to provide constant heart pump motor speed at a particular performance level. Operating the motor (e.g., contained in motor housing 102 of FIG. 1) of the heart pump system to maintain a constant rotor speed, as is desirable in many medical situations, generally requires supplying the motor with varying amounts of current because the load on the motor varies during the different stages of the cardiac cycle of the heart. Accordingly, when the differential pressure in a patient's heart changes, the motor current will also change to keep the rotor speed constant. For example, when the flow rate of blood into the aorta increases (e.g., during systole), the current required to operate the motor increases. This change in motor current can thus be used to help characterize cardiac function as will be discussed further in relation to the following figures. The motor current signal may be derived from measurements from a sensor on the pump motor within the pump, or within the processor or controller itself. Even if differential pressure is not known at a given time, the rotor speed at that time will be known and motor current will be tuned to ensure the rotor speed is stable. The systems and method described herein build a relationship between past motor current and differential pressure signal data for a particular heart pump system during a first period of time, then use this relationship to determine an estimate differential pressure signal from newly-received motor current data during a second period of time. The motor current/differential pressure signal relationship is determined for a specific heart pump system and is indicative of the characteristics of that specific heart pump system.

Once the relationship between the motor current and differential pressure signal has been determined, the motor current is used to determine an estimate of differential pressure signal. For a given motor current value, however, there could be two possible corresponding differential pressure signal values, a first phase (also referred to herein as "Phase A") value and a second phase (also referred to herein as "Phase B") value. The systems and methods described herein may determine whether the heart pump system is in Phase A or Phase B, and determine the estimate of the differential pressure signal accordingly, as will be described further below.

Because the estimate of time-varying differential pressure can be determined using the motor current and the relationship, the systems and methods described herein may be particularly useful if the differential pressure sensor fails and the measured differential pressure signal data is unavailable or is unreliable due to drift, as described below in relation to FIGS. 14-15. In some aspects, the estimate of time-varying differential pressure may be determined in response to determining the differential pressure sensor has failed. In some aspects, if the differential pressure sensor fails, the heart pump system may set off an alarm. In some aspects, the estimate of the differential pressure may be determined regardless of whether the differential pressure sensor has failed. By comparing the measured differential pressure signal to the estimated differential pressure signal, the systems and methods described herein may also be used to determine that the measured differential pressure signal is drifting and needs to be re-calibrated.

The heart pump system is at least partially inserted within the heart of a patient. Heart pump systems compatible with the present disclosure are disclosed in U.S. Patent Application Publication No. 2018-0078159-A1, the contents of which are hereby incorporated by reference in their entirety. Generally, any other heart pump system or system for obtaining physiological data from a patient may be used with the present disclosure. For example, the differential pressure signal and motor current data may be displayed on an interface that is connected to or is part of a heart pump system like the Automated Impella Controller (AIC). Raw features may be extracted from heart pump system signals. The heart pump system may have a display, such as a placement screen that displays real time operating data for the heart pump system. Such a placement screen may display the differential pressure signal and motor current waveforms as well as the maximum/minimum and average values for each waveform in the central display area of the screen.

In some implementations, the systems and methods described herein may relate to the Impella 5.0 device of the IMPELLA® family of devices (Abiomed, Inc., Danvers MA).

FIG. 1 shows an illustrative heart pump system, inserted into a blood vessel of a patient and configured to estimate cardiovascular parameters, according to certain implementations. The heart pump system 100 may operate within a heart, partially within the heart, outside the heart, partially outside the heart, partially outside the vascular system, or in any other suitable location in a patient's vascular system. The heart pump system may be considered "in position" when cannula 173 is placed across the aortic valve such that a blood inlet (e.g., blood inlet 172) to the pump is within the left ventricle and an outlet (e.g., outlet openings 170) from the pump is within the aorta. The heart pump system 100 includes a heart pump 106 and a control system 104. All or part of the control system 104 may be in a controller unit separate/remote from the heart pump 106. In some implementations, the control system 104 is internal to the heart pump 106. The control system 104 and the heart pump 106 are not shown to scale. The pump system 100 includes an elongate catheter body 105, a motor housing 102 and a drive shaft in which a pump element is formed. The pump 100 includes a pump housing 134, and a motor housing 102 coupled to a cannula 173 at a distal end 111 of the motor housing 102. An impeller blade on the drive shaft may be rotated within a pump housing 134 to induce a flow of blood into the cannula 173 at a suction head 174. The suction head 174 provides a blood inlet 172 at the distal end portion 171 of the cannula 173. The flow 109 of blood passes through the cannula 173 in a first direction 108 and exits the cannula 173 at one or more outlet openings 170 of the cannula 173.

The rotation of the drive shaft within the pump housing 134 may also rotate a pump element within a bearing gap. A hemocompatible fluid may be delivered through the elongate catheter 105 through the motor housing 102 to a proximal end portion of the cannula 173 where the fluid is pressurized by the rotation of a pump element. The flow of hemocompatible fluid has a second direction 122 through the bearing gap of the pump. After exiting the bearing gap, the hemocompatible fluid may follow flow direction 123 and become entrained in the flow of blood and flows into the aorta with the blood.

The heart pump 100 is inserted into a vessel of the patient through a sheath 175. The pump housing 134 may enclose the rotor and internal bearings and may be sized for percutaneous insertion into a vessel of a patient. In some implementations, the pump may be advanced through the vasculature and over the aortic arch 164. Although the pump is shown in the left ventricle, the pump may alternatively be placed in the right heart, such that the blood is pumped from the patient's inferior vena cava or right atrium, through the right ventricle into the pulmonary artery.

A flexible projection 176 may also be included at a distal end portion 171 of the cannula 173, distal to the suction head 174, in order to position the heart pump 100 optimally in a vessel or chamber of the heart. The flexible projection 176 may prevent the suction head 174 from approaching the wall of the vessel where it may become stuck due to suction. The flexible projection 176 may extend the pump 100 mechanically, but not hydraulically, as the flexible projection 176 may be non-sucking. In some implementations, the flexible projection may be formed as a pigtail. In some aspects, the pump need not include a flexible projection.

The elongate catheter 105 houses a connection 126 that may comprise a fluid supply line and may also house electrical connection cables. The connection 126 may supply a hemocompatible fluid to the pump from a fluid reservoir that may be contained within control system 104.

The control system 104 includes controller 182 controls pump 106, including, for example, controlling power to the motor or controlling the motor speed may also include a heart parameter estimator 116. In some implementations, the control system 104 includes display screens to show measurements such as differential pressure signal and motor current. The control system 104 may include circuitry for monitoring the motor current for drops in current indicating air in the line, changes in differential pressure signal, flow position, suction, or any other suitable measurement. The control system 104 may include warning sounds, lights or indicators to alert an operator of sensor failures, disconnects or breaks in the connection 126, or sudden changes to patient health.

The control system 104 can include a current sensor (not shown). The controller 182 supplies current to the motor 108 by the connection 126 such as through one or more electrical wires. The current supplied to the motor 108 via the connection 126 is measured by the current sensor. The load that the motor of a mechanical pump experiences is pressure head, or the difference between the aortic and left ventricular pressure. The heart pump 106 experiences a nominal load during steady state operation for a given pressure head, and variations from this nominal load are a result of changing external load conditions, for example the dynamics of left ventricular contraction. Changes to the dynamic load conditions alter the motor current required to operate the pump rotor at a constant, or substantially constant, speed. The motor may operate at a speed required to maintain the rotor at a set speed. As a result, and as further described below, the motor current drawn by the motor to maintain the rotor speed can be monitored and used to understand the underlying cardiac state. The cardiac state can be even more precisely quantified and understood by simultaneously monitoring the pressure head during the cardiac cycle using a pressure sensor 112. The heart parameter estimator 185 receives current signals from the current sensor as well as pressure signals from the pressure sensor 112. The heart parameter estimator 185 uses these current and pressure signals to characterize the heart's function. The heart parameter estimator 185 may access stored look-up tables to obtain additional information to characterize the heart's function based on the pressure and current signals. For example, the heart parameter estimator 185 may receive an aortic pressure from the pressure sensor 112, and using look-up tables, may use the aortic pressure to determine a delta pressure.

The pressure sensor is a flexible membrane integrated into the cannula 172. As described above, one side of the sensor is exposed to the blood pressure on the outside of the cannula and the other side is exposed to the pressure of the blood inside of the cannula. The sensor generates an electrical signal (the differential pressure signal) proportional to the difference between the pressure outside the cannula and the pressure inside, which may be displayed by the heart pump system. When the heart pump system is placed in the correct position across the aortic valve, the top (outer surface) of the sensor is exposed to the aortic pressure and the bottom (inner surface) of the sensor is exposed to the ventricular pressure. Therefore, the differential pressure signal is approximately equal to the difference between the aortic pressure and the ventricular pressure.

Figure 2:
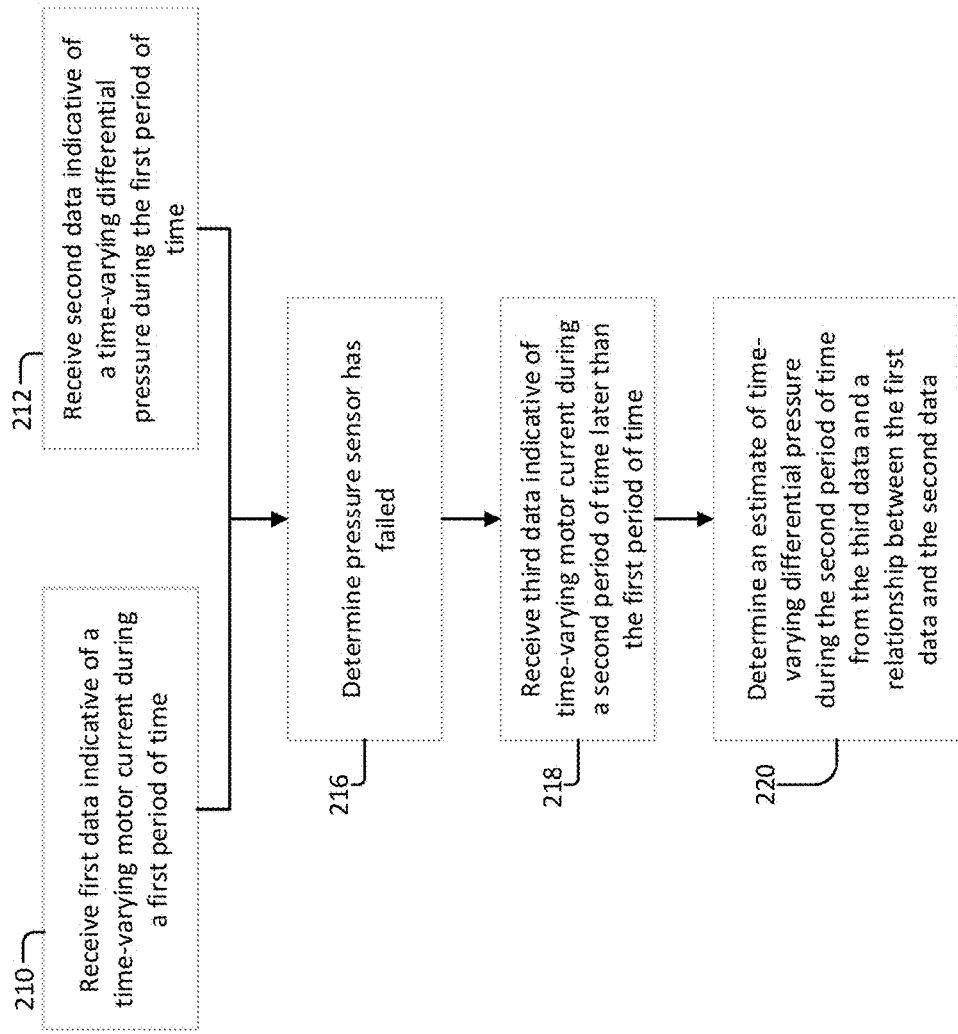
FIG. 2 shows a process for estimating a position of a heart pump system in a patient, according to certain implementations.

FIG. 2 shows a process 200 for determining an estimate of time-varying differential pressure based on motor current, according to certain implementations. The process 200 can be performed using any suitable heart pump system, such as that described in FIG. 1. In step 210, first data indicative of a time-varying motor current during a first period of time is received. The first data (also referred to as motor current data) may be part of a motor current signal. The motor current data describes current delivered to a motor in a heart pump system, as described above. For example, the motor may be operated at a rotational speed necessary to maintain a constant or substantially constant rotational speed of the rotor. The current may be measured using a current sensor (e.g., the current sensor described in relation to FIG. 1) or by any other suitable means. In step 212, second data indicative of a time-varying differential pressure during the first time is received. The second data (also referred to as differential pressure signal data) may be part of a differential pressure signal. In some implementations, the differential pressure signal data describes changes in pressure measured by a differential pressure sensor (e.g., pressure sensor 112). The differential pressure sensor may be an optical pressure sensor, an electrical pressure sensor, a MEMS sensor, or any other suitable pressure sensor. The differential pressure signal can be used by clinicians to monitor the position of the heart pump relative to the patient's aortic valve. The differential pressure signal and motor current signal may be displayed to a clinician or other operator of the heart pump system. In some aspects, the first data and the second data are received or acquired from the heart pump system, which may be located at least partially within the patient's heart during the first time period.

A relationship between differential pressure and motor current for the heart pump system is determined. The relationship is determined using training data, which may comprise the motor current data and differential pressure signal data received in steps 210 and 212, as described above. In some aspects, the motor current data and differential pressure signal data are acquired while the heart pump system is operating at a single P-level. P-level is the performance level of the heart pump system and related to flow control of the system, presenting the motor speed. As P-level increases, the flow rate, motor current, and revolutions per minute associated with the heart pump system increase. For example, the motor current data and differential pressure signal data may each comprise 1000 sample points (the frequency of real-time data collection is 25 Hz) corresponding to the same 40 second period of time, during which the heart pump system was operating at P-level P-8.

The systems and methods described herein may calculate a model to represent the training data. In some aspects, the systems and methods described herein calculate a representative relationship between the motor current and the differential pressure signal by plotting the differential pressure signal data values with respect to the motor current data values, and/or determining a multilinear regression of the resulting curve. This curve and the associated multilinear regression are representative of the relationship between motor current and differential pressure signal for the heart pump system from which the motor current data and differential pressure signal data were acquired. This curve and the associated multilinear regression may be indicative of operating characteristics of the specific heart pump system from which the first data and second data (relating to motor current and differential pressure respectively) were acquired. For example, these operating characteristics may include minimum and maximum differential pressure, minimum and maximum motor current, and the inflection point between the first and second phases of operation at a given performance level.

In optional step 216, the systems and methods described herein determine the pressure sensor has failed. In some aspects, the systems and methods may determine the pressure sensor has failed when the system no longer receives any differential pressure signal data, or when no data is received from the differential pressure sensor during the second period of time. In some aspects, the systems and methods described herein may determine the pressure sensor needs to be re-calibrated, as described in further detail below in relation to FIGS. 14-15. After determining the pressure sensor needs to be re-calibrated, an estimate of differential pressure signal, such as that described below in step 220, may be relied on for further calculations such as suction, flow, and position, rather than the measured differential pressure signal.

In step 218, third data indicative of time-varying motor current during a second period of time later than the first period of time is received. The third data (referred to hereinafter as additional motor current data) is measured by the same sensor of the same heart pump system as described above in relation to the motor current data of step 210. The additional motor current data may represent a period of time after that represented by the motor current data received in step 210. In some aspects, the additional motor current data may have been acquired at a different P-level than the motor current data of step 210. For example, the additional motor data may represent a 2 second period of time during which the heart pump system was operating at P-level P-6.

In step 220, an estimate of time-varying differential pressure during the second period of time is determined from the third data and the relationship between the first data (motor current data) and the second data (differential pressure signal data) described above. If the P-level used for collection of the motor current data and differential pressure signal data is different from that used for collection of the additional motor current data, the relationship must be scaled to account for the change in P-level, as described below in relation to FIG. 4. Once the relationship has been scaled, the systems and methods described herein determine whether, for the additional motor current data, the heart pump system is in "Phase A" or "Phase B", as described below in relation to FIG. 3. Phase determination is dependent on motor current values during the start and end of the diastolic phase of a cardiac cycle, which depend on patient pressure and P-level. Then, each additional motor current data value is mapped to a corresponding Phase A or Phase B differential pressure signal value. In some implementations, this simulation occurs in near real time and can be displayed to an operator of the heart pump system. If the pressure sensor has failed, the estimated differential pressure signal may be displayed instead of the measured differential pressure signal, allowing a clinician to still view differential pressure signal data in spite of the pressure sensor failure. In some aspects, the heart pump system may display a notification indicating that the differential pressure sensor has failed or is unreliable. In some aspects, the heart pump system may display a notification indicating that the estimate of time-varying differential pressure is simulated and/or that the heart pump system is displaying the estimate of differential pressure signal, rather than the measured differential pressure signal.

An accurate differential pressure signal can be used not only to properly position a heart pump system within a patient, but also to determine additional metrics such as flow, position, suction, drift, and cardiac output (which can be calculated from flow). Flow is the flow rate of blood through the pump in the heart pump system. Flow can be used to calculate cardiac output for a patient and provides a measure of the mechanical assistance provided to the heart by the heart pump. The blood flow through a healthy heart averages about 5 liters/minute, and the blood flow through the heart pump system can be a similar or different flow rate. Suction occurs when the blood volume available for the heart pump system is inadequate or restricted. Suction is highly important to monitor, as it limits the amount of support the heart pump system can provide and may indicate the heart pump is blocked, for example, if the inlet area of the pump is lodged against patient tissue. Position is the actual positioning of the heart pump within the patient's heart, which is important to the proper operation of the heart pump system. Drift is when the measured differential pressure signal drifts up or down from expected or consistent values. If the differential pressure signal begins to drift, the pressure sensor may need to be recalibrated. In some implementations, the system may determine that pressure sensor needs to be recalibrated and the system may display a warning or signal to the user to re-calibrate accordingly or may automatically recalibrate the sensor.

As mentioned above, the differential pressure signal may be used to determine whether the heart pump system is properly positioned in a patient's heart. When the heart pump system is correctly positioned across the aortic valve, the changes in pressure associated with the cardiac cycle results in a pulsatile differential pressure signal. When the heart pump system is not properly places across the aortic valve, or when it is fully in the aorta or fully in the ventricle, the pressures outside and inside the cannula are the same throughout the cardiac cycle. As a result, the pressure on either side of the sensor membrane is the same, resulting in a flat differential pressure signal. If, however, the differential pressure signal is unreliable, it may difficult for clinicians to determine if the system is positioned correctly, in which case an estimated differential pressure signal would be very useful.

The heart pump system may be operated to achieve the maximum possible flow without causing suction. Flow rate can vary due to incorrect positioning or suction. If the blood volume available for the heart pump is inadequate or restricted, the heart pump system may trigger a suction alarm. Suction limits the amount of support that the heart pump system can provide to the patient, resulting in a decrease in arterial pressure and cardiac output; can damage blood cells, leading to hemolysis; and may also be an indicator of right heart failure. Thus, it is important to monitor suction during operation of the heart pump system.

Figure 3:
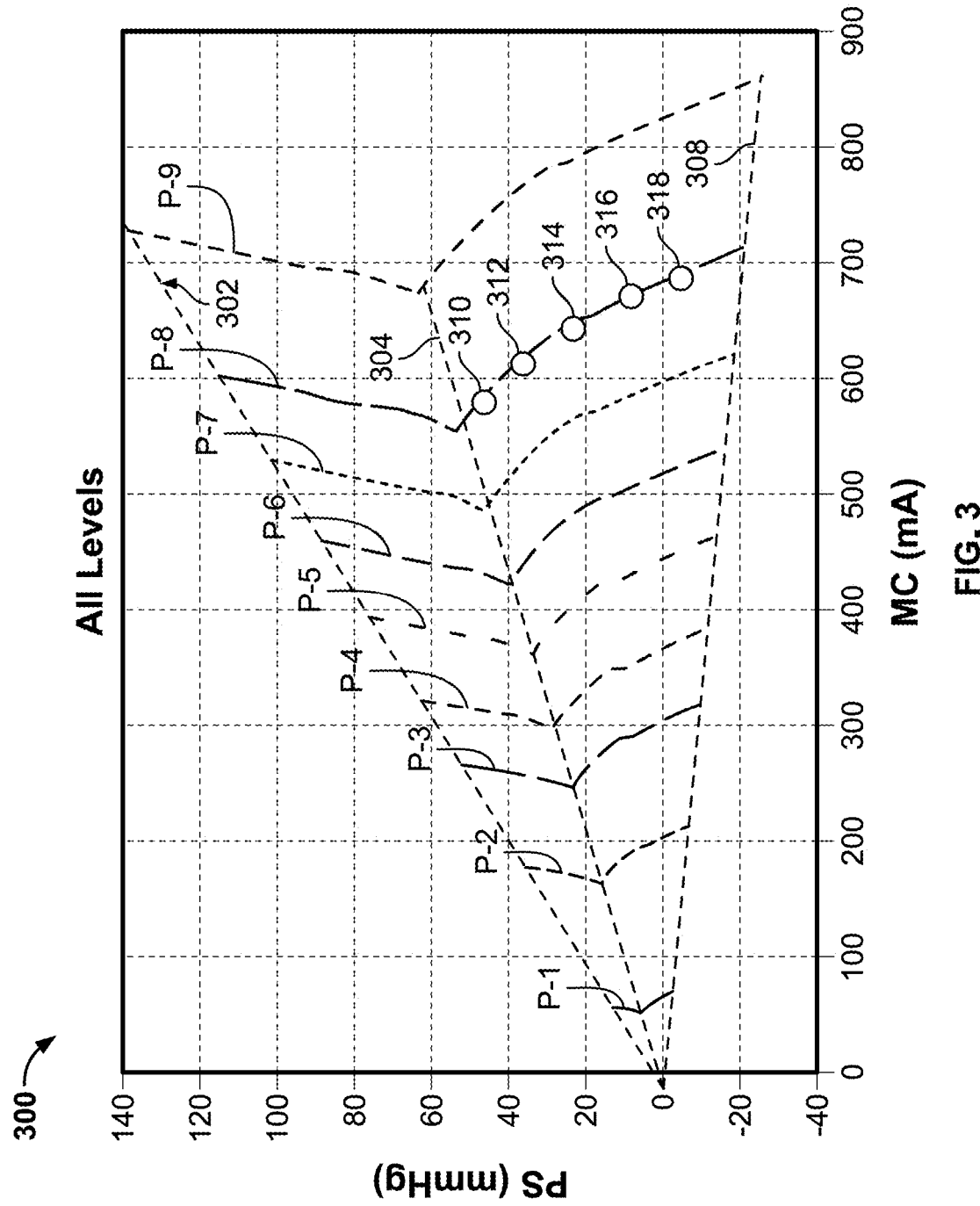
FIG. 3 shows a plot of differential pressure signal versus motor current for a heart pump system operating at a range of performance levels, according to certain implementations.
Figure 4:
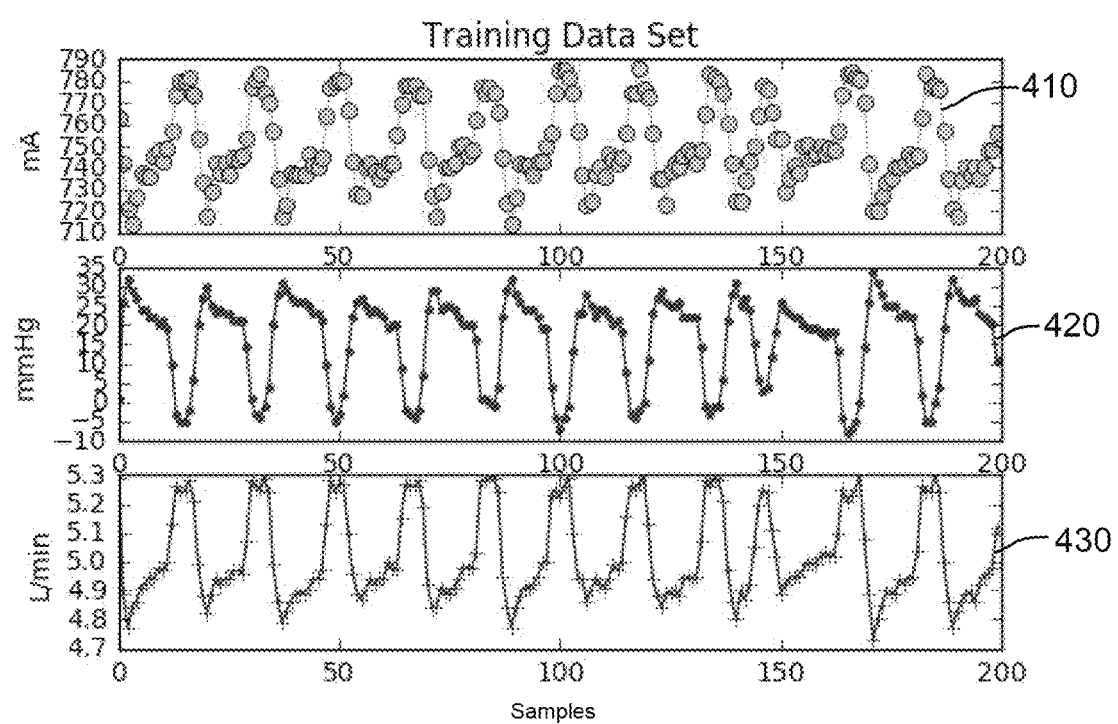
FIG. 4 shows plots of motor current, differential pressure signal, and flow over a period of time, according to certain implementations.
Figure 5:
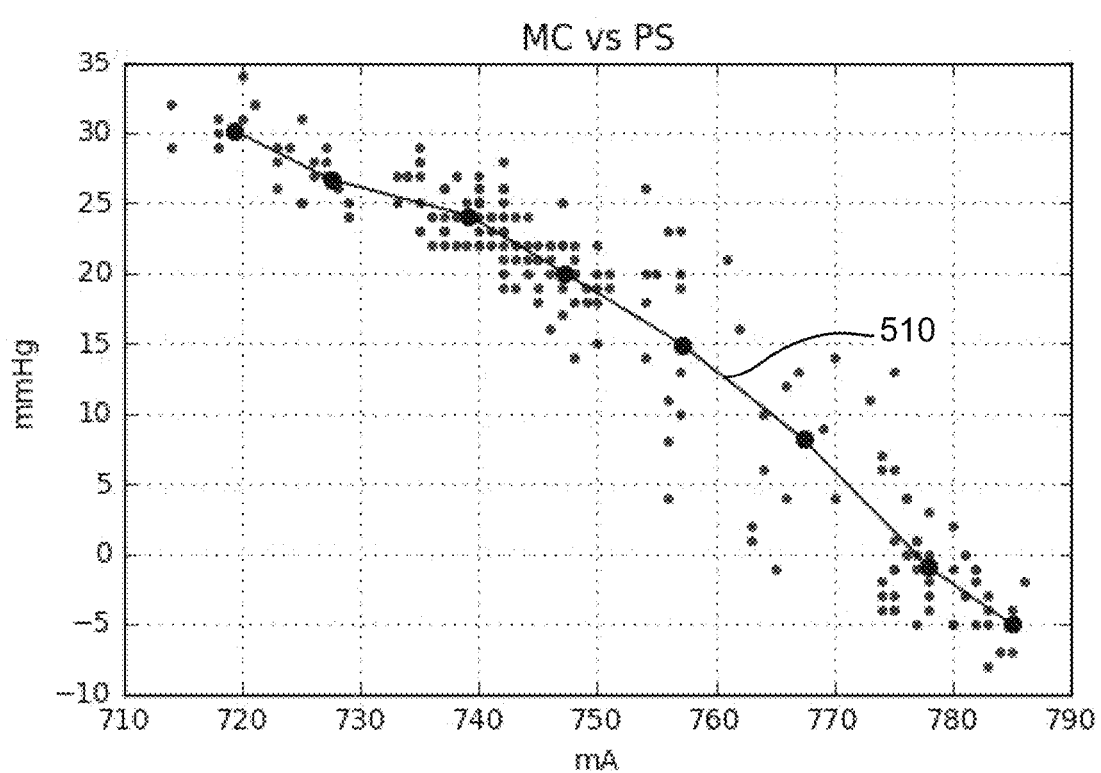
FIG. 5 shows a plot of differential pressure signal versus motor current for a heart pump system, according to certain implementations.
Figure 6:
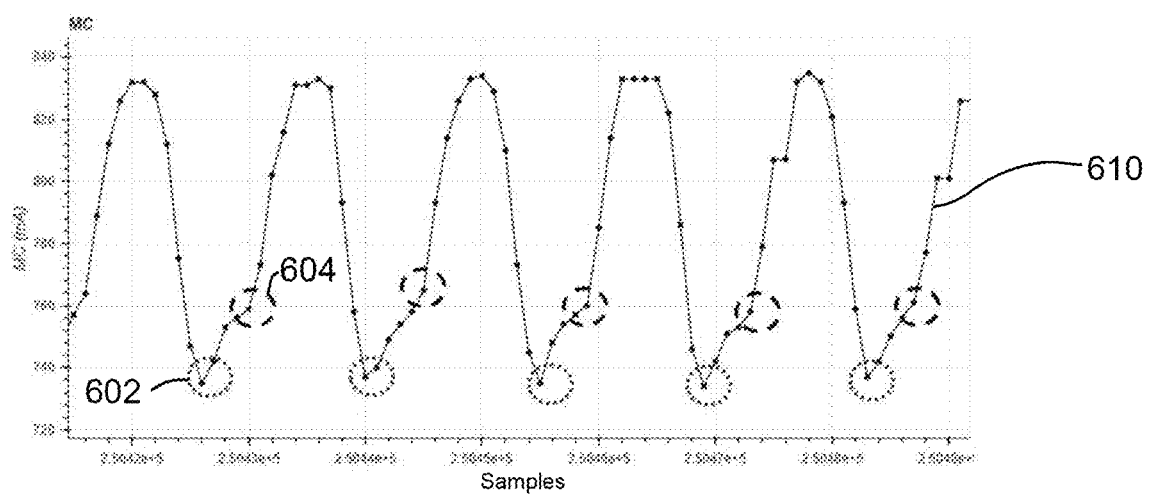
FIG. 6 shows a plot of motor current over time for a first phase, according to certain implementations.
Figure 7:
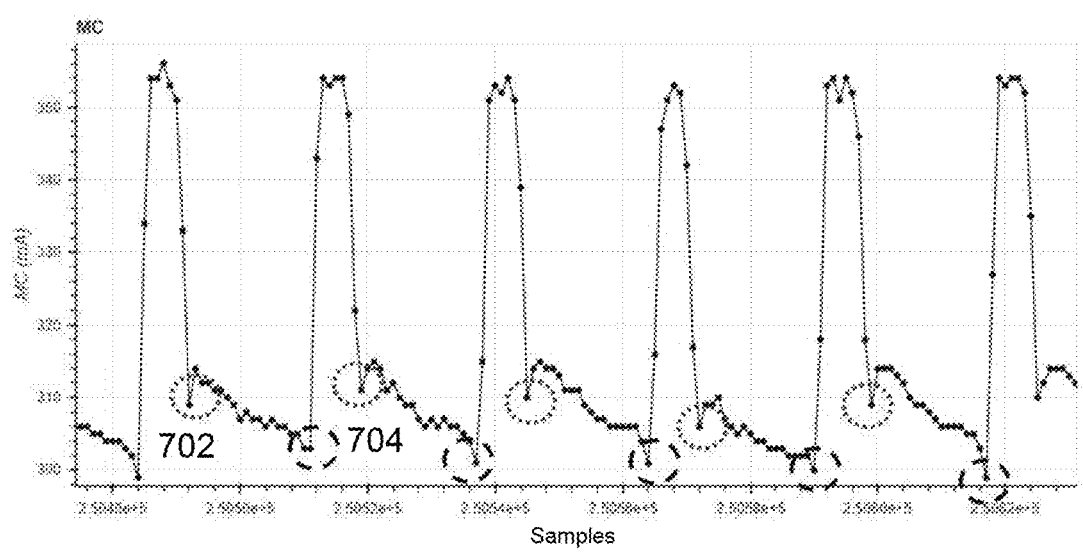
FIG. 7 shows a plot of motor current over time for a second phase, according to certain implementations.
Figure 8:
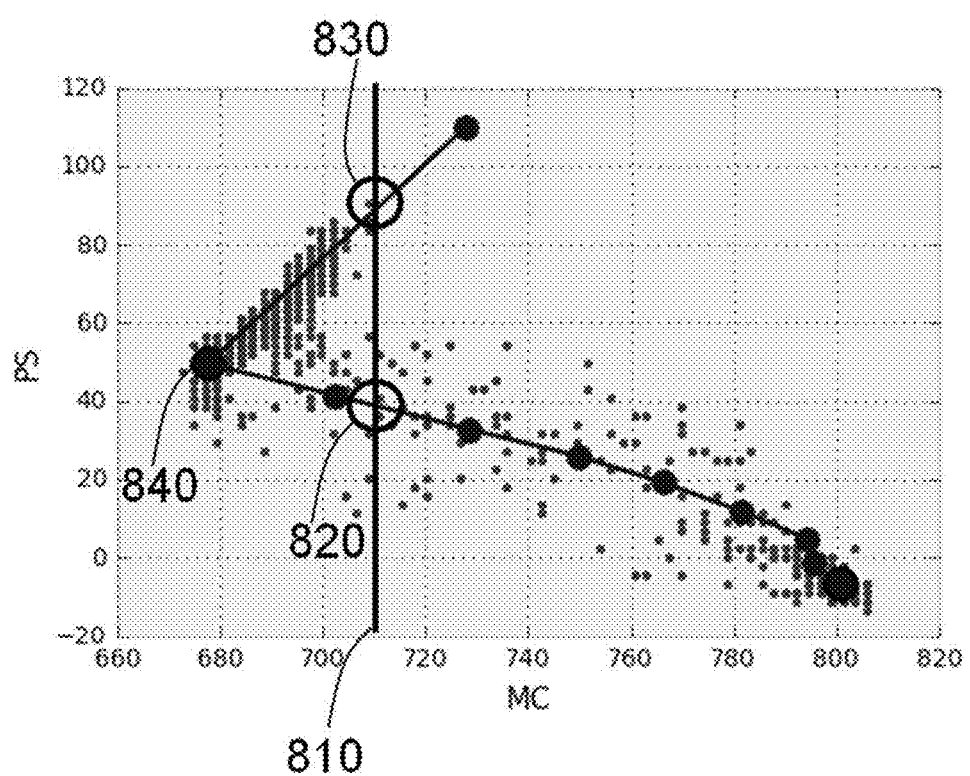
FIG. 8 shows a plot of differential pressure signal versus motor current for a heart pump system for first and second phases, according to certain implementations.
Figure 9:
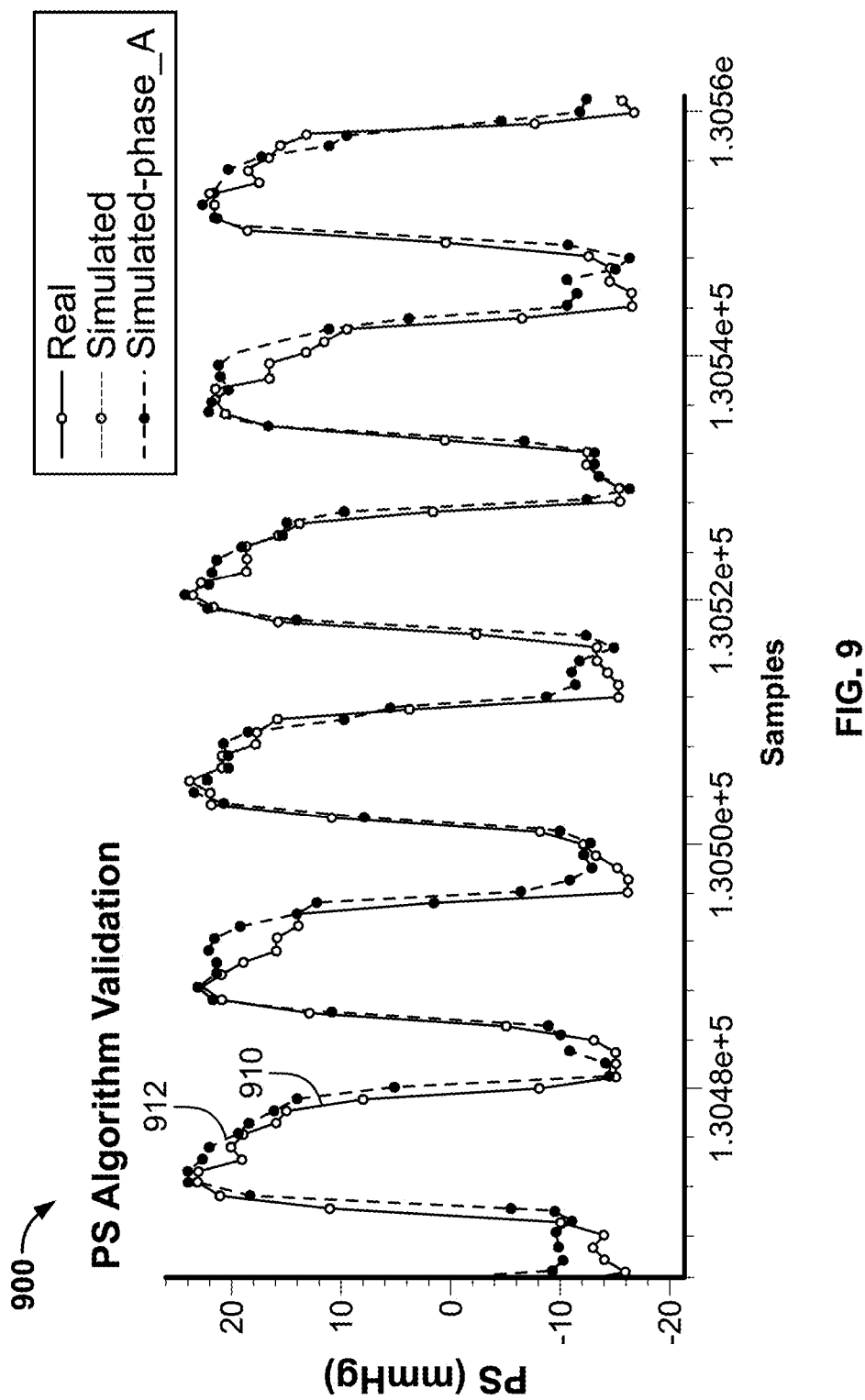
FIG. 9 shows a plot of real, simulated and simulated first phase differential pressure signal during first phase operation over a period of time, according to certain implementations.
Figure 10:
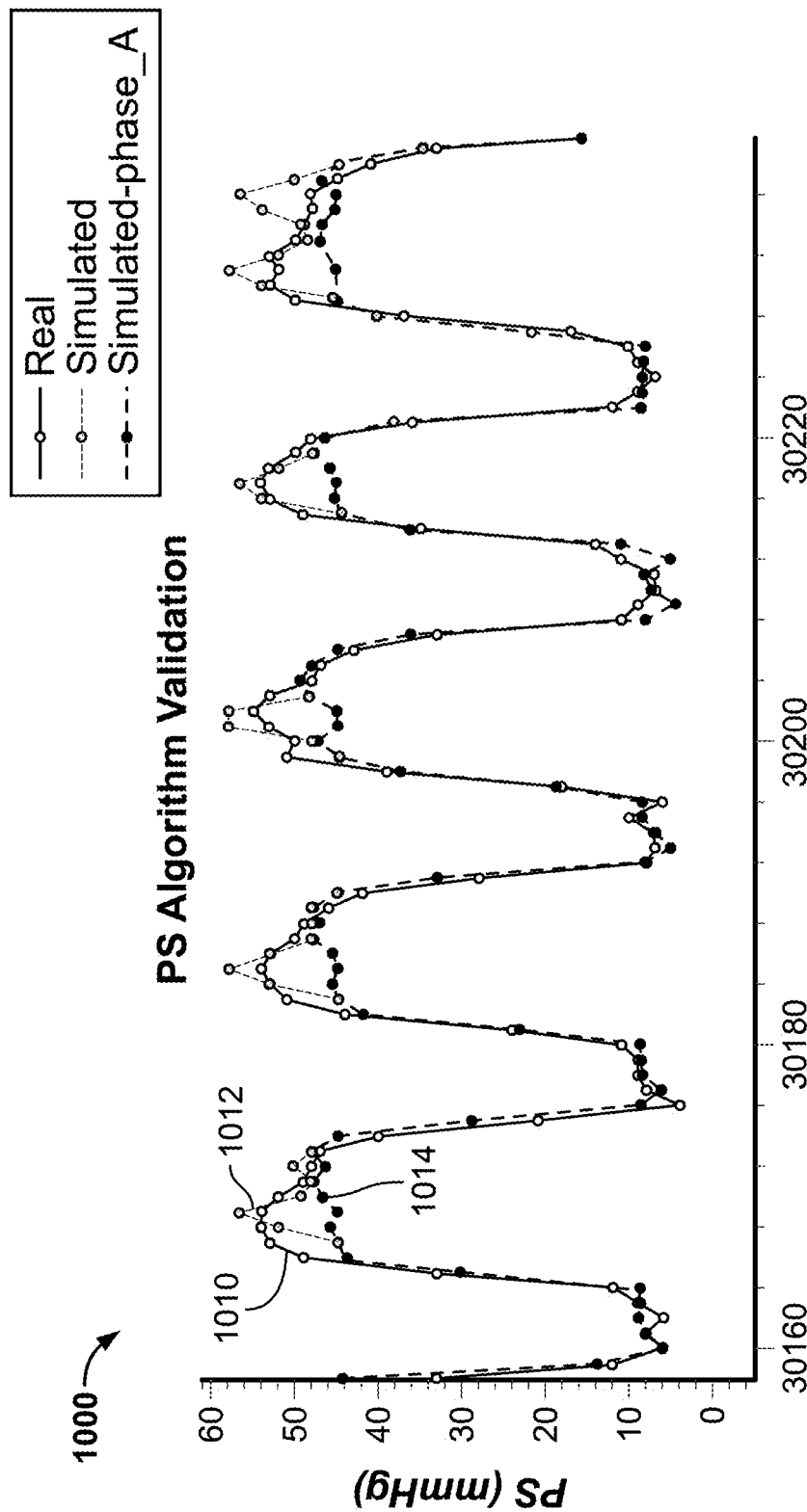
FIG. 10 shows a plot of real, simulated and simulated first phase differential pressure signal during second phase operation over a period of time, according to certain implementations.
Figure 11:
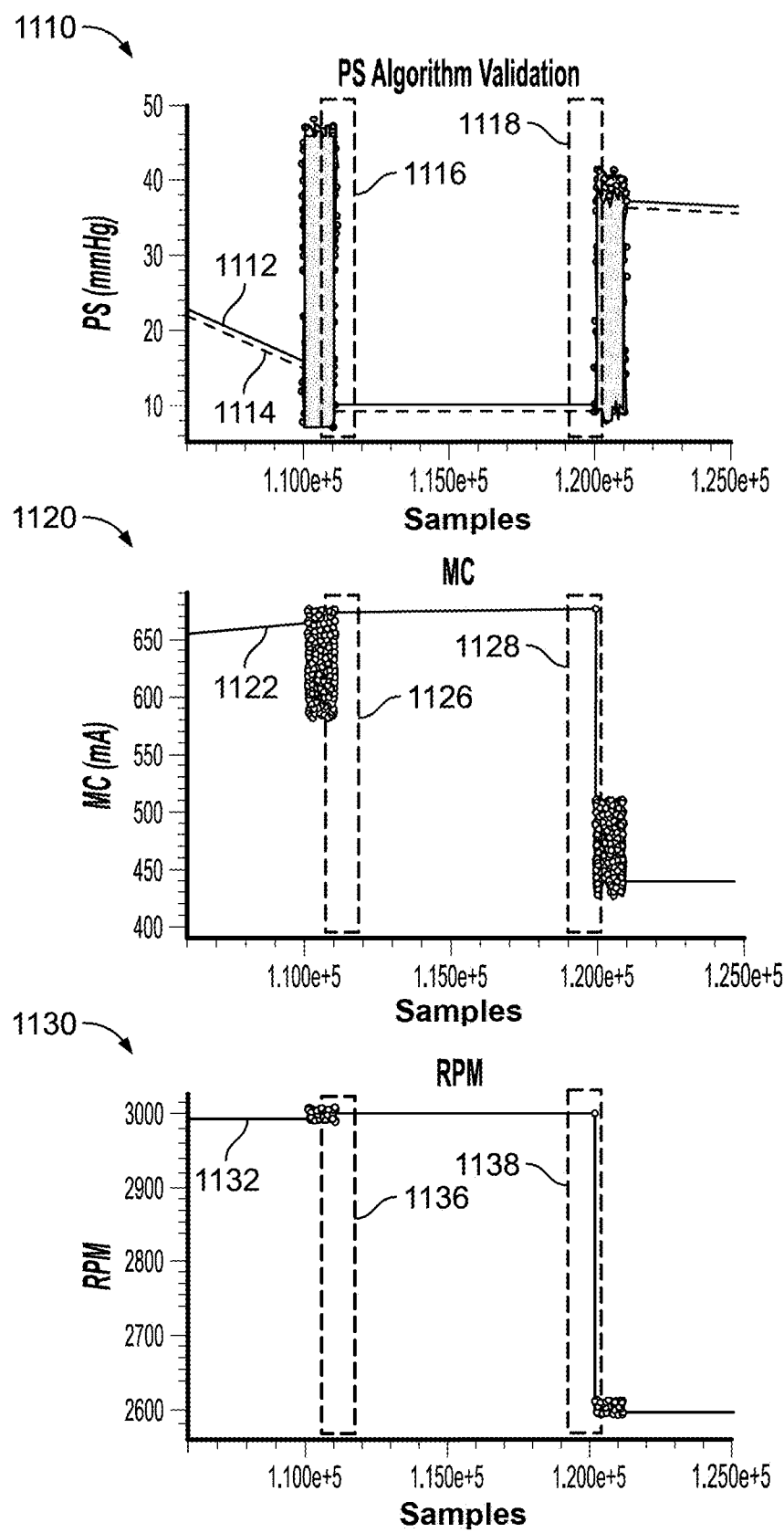
FIG. 11 shows plots of differential pressure signal, motor current and rotations per minute (RPM) for a heart pump system, when the performance level of the heart pump system changes between two levels, according to certain implementations.
Figure 12:
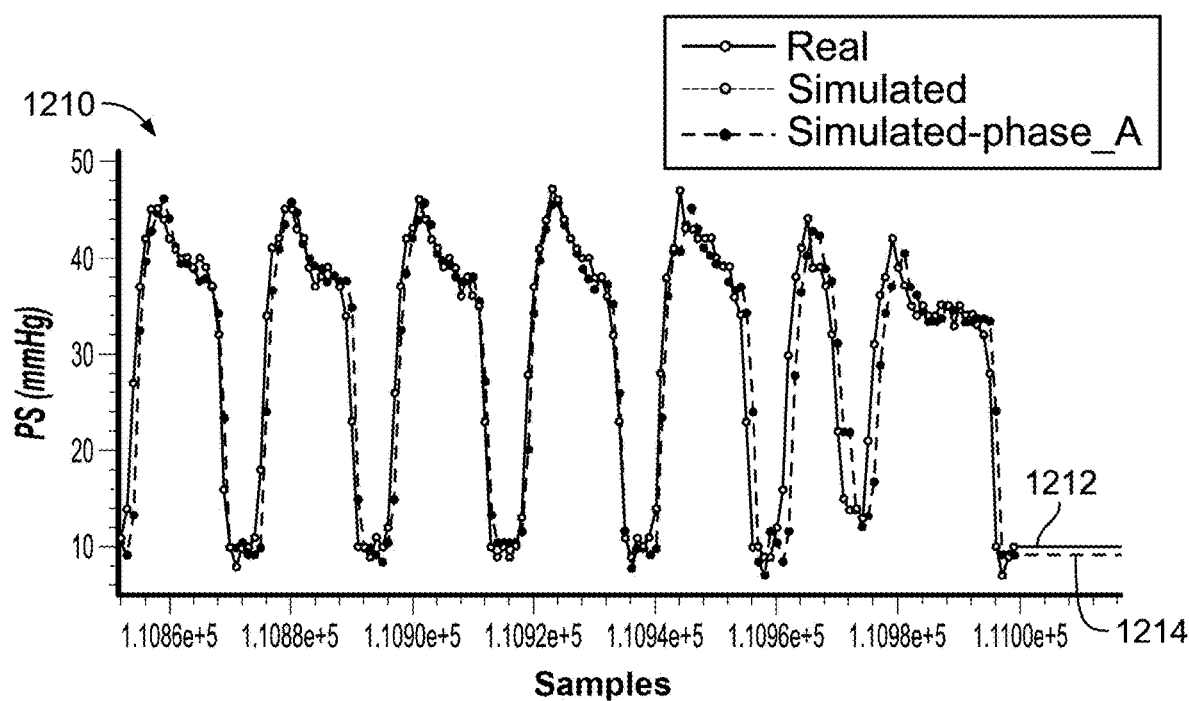
FIG. 12 shows plots of differential pressure signal and motor current at a first performance level over a period of time, according to certain implementations.
Figure 12:
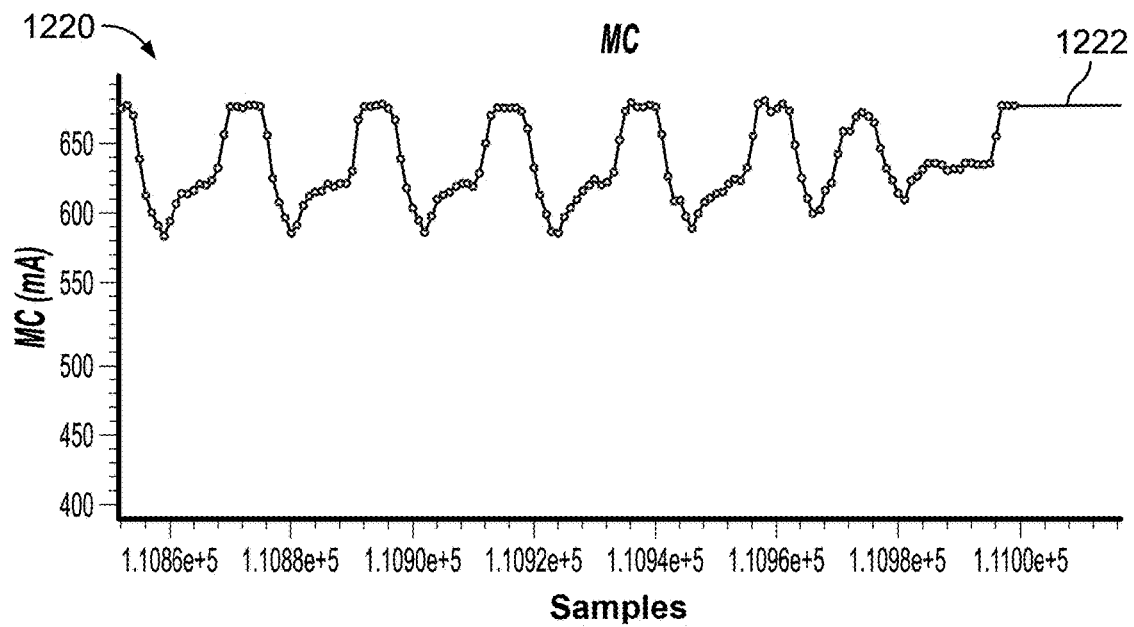
Figure 13:
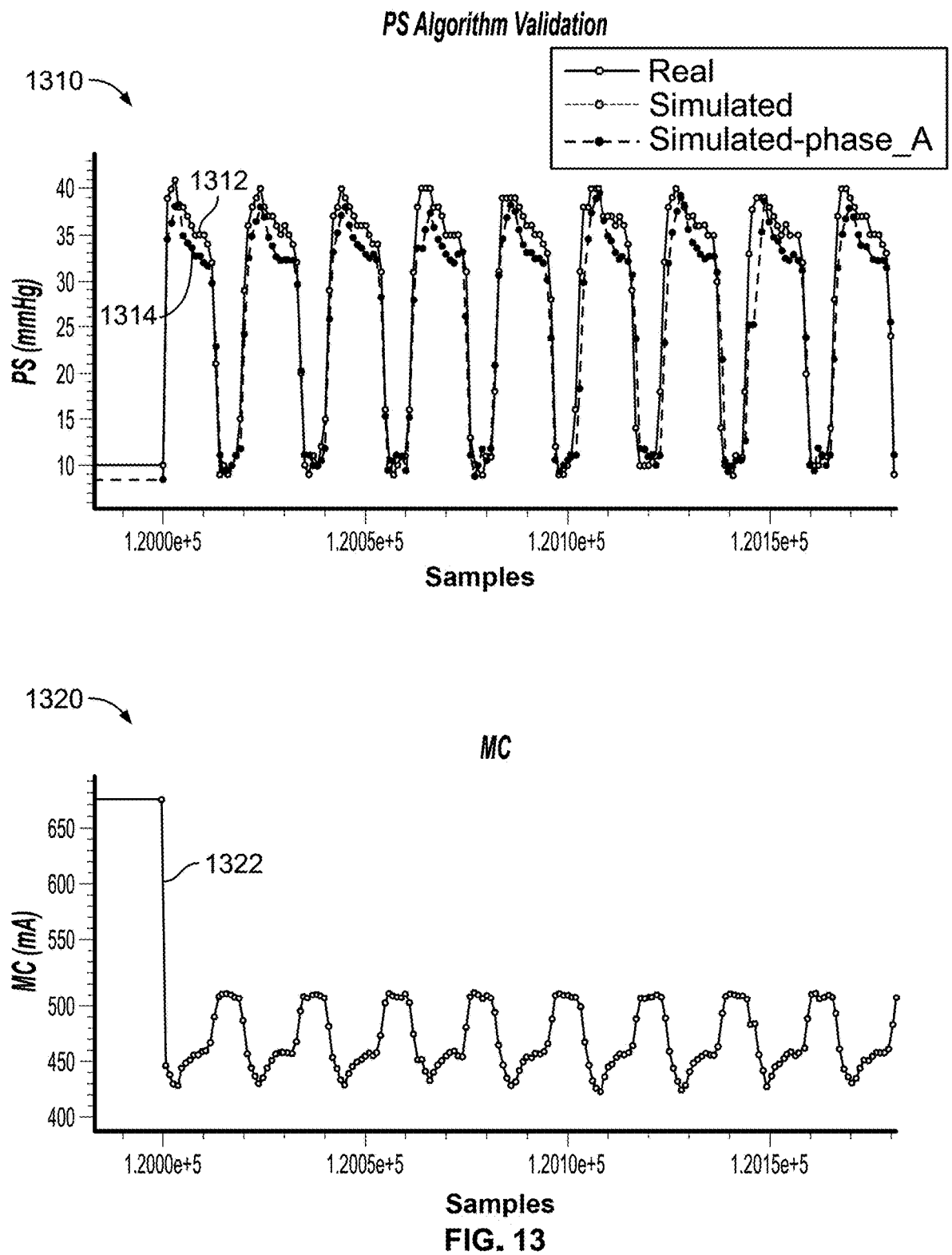
FIG. 13 shows plots of differential pressure signal and motor current at a second performance level over a period of time, according to certain implementations.
Figure 16:
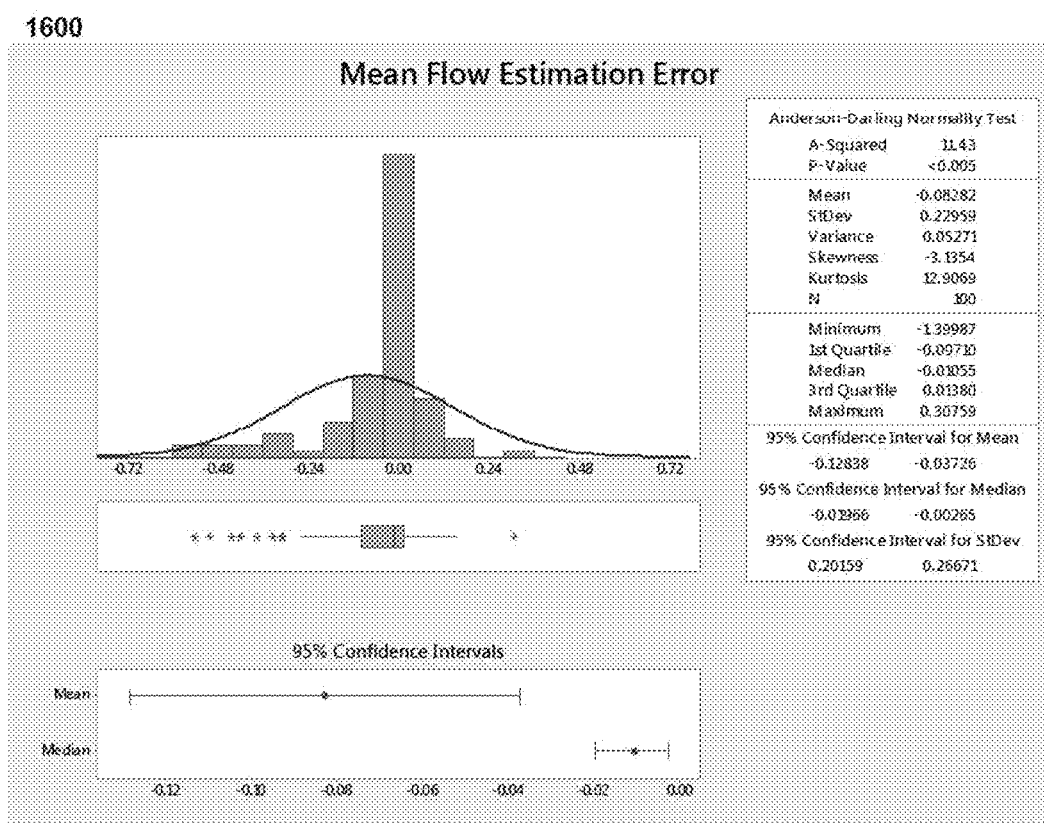
FIG. 16 shows a histogram of mean flow estimation error, according to certain implementations.
Figure 17:
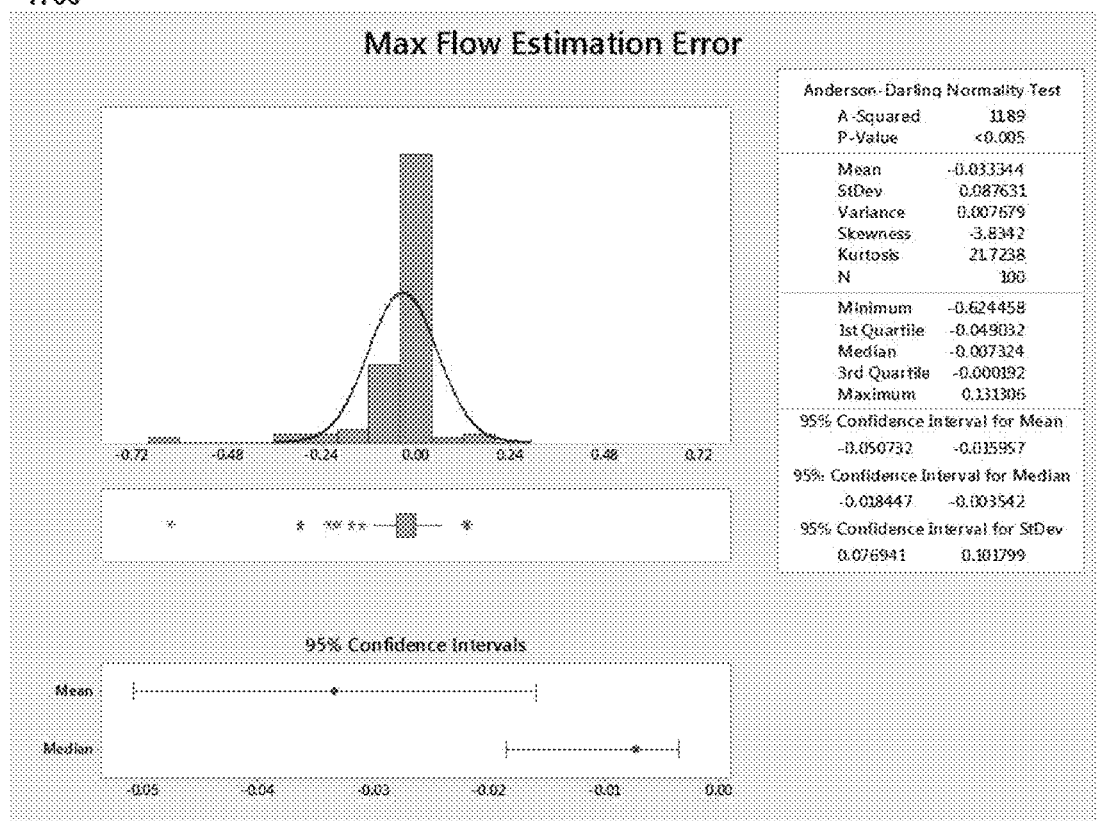
FIG. 17 shows a histogram of maximum flow estimation error, according to certain implementations.
Figure 18:
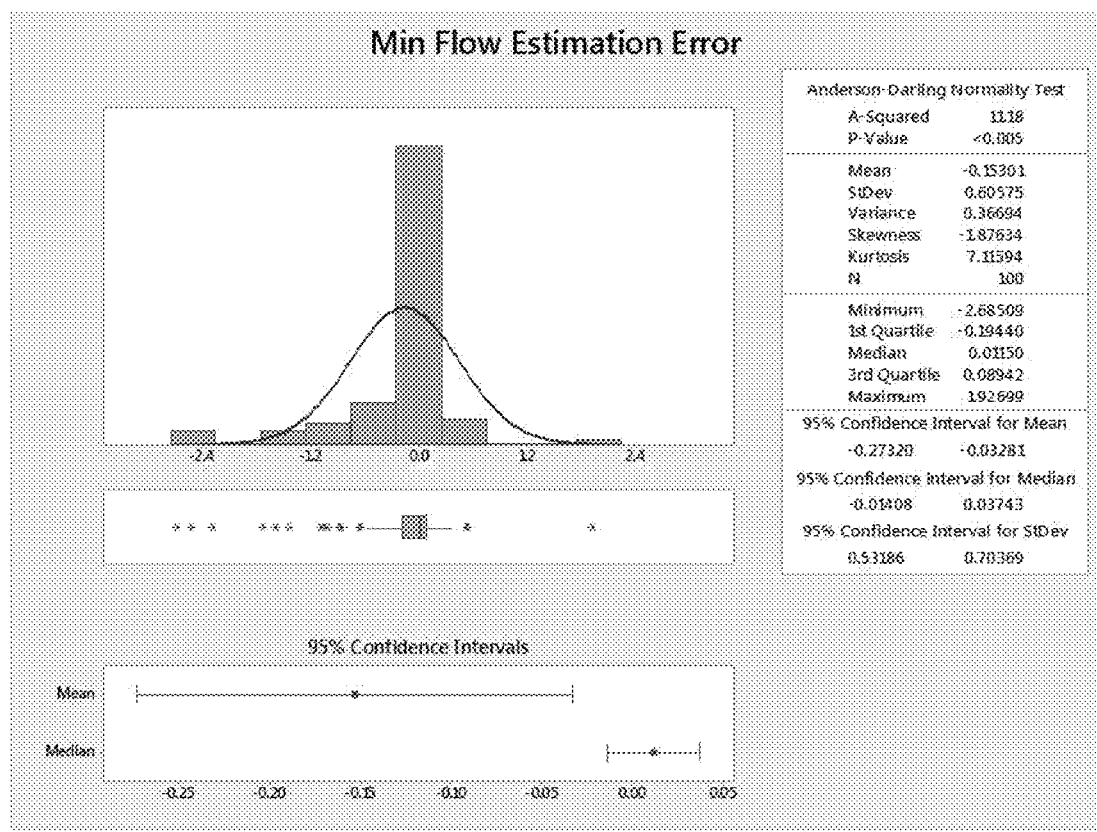
FIG. 18 shows a histogram of minimum flow estimation error, according to certain implementations.

FIGS. 3-18 further illustrate various implementations and example results of the present disclosure. FIG. 3 shows an example of the relationship between differential pressure and motor current for a specific heart pump at different performance levels. The curves shown in FIG. 3 were calculated using motor current and differential pressure signal data, such as that described above in relation to steps 210 and 212. FIG. 4 shows an example of the training data described above in relation to steps 210 and 212. FIG. 5 shows an example of the relationship between differential pressure and motor current for a specific heart pump at a single performance level, operating in the first phase only. FIG. 6 shows an example of motor current data, such as that described in relation to step 210 above, during operation in the first phase. FIG. 7 shows an example of motor current data, such as that described in relation to step 210 above, during operation in the second phase. FIG. 8 shows an example of the relationship between differential pressure and motor current for a specific heart pump at a single performance level, for both the first phase and the second phase. The curve shown in FIG. 8 may be an example of one of the multiple curves shown in FIG. 3. FIGS. 9-10 show measured differential pressure signal data and an estimate of differential pressure signal, such as that described above in relation to steps 218 and 220 respectively. FIG. 11 shows measured differential pressure signal, an estimate of differential pressure signal (such as that described in step 220), motor current (such as that descried in step 218), and rotations per minute of the heart pump motor's rotor (such as that described above in relation to FIG. 1). FIGS. 12-13 show measured differential pressure signal, an estimate of differential pressure signal (such as that described in step 220), and motor current (such as that described in step 218), resulting from training at a first P-level and testing in the first and a second P-level. FIGS. 14-15 show the drift of measure differential pressure signal in comparison to motor current data (such as that in step 210 or step 218) and an estimate of differential pressure signal (such as that in step 220). As will further be described in relation to FIGS. 14-15 below, the estimated differential pressure signal may also be used to determine whether the differential pressure signal is drifting or has drifted, and whether the sensor needs to be re-calibrated. FIGS. 16-18 show results of the efficacy of the estimate of flow rate calculated using estimated differential pressure signal (such as that in step 220) when compared to flow rate calculated using measured differential pressure signal.

FIG. 3 shows a plot 300 of differential pressure signal versus motor current for a heart pump system operating at nine different performance levels, according to certain implementations. The y-axis of plot 300 represents differential pressure signal in mmHg, while the x-axis represents motor current in mA. Each curve P-1 through P-9 is indicative of a representative curve for the same heart pump system operating at different performance level, or P-level (e.g., curve P-1 corresponds to operating performance level P-1), which relates to flow control of the heart pump system. Higher P-levels correspond to higher flow rates and revolutions per minute associated with the heart pump system.

As is depicted in FIG. 3, the relationship between differential pressure and motor current for a heart pump system scales across performance levels. Accordingly, if the relationship between differential pressure and motor current for a given heart pump system is determined at a first P-level (e.g., P-8), the relationship between differential pressure and motor current for the heart pump system may be scaled to determine the relationship between differential pressure and motor current for that heart pump system at a second P-level (e.g., P-6). For example, in the case shown in FIG. 3, differential pressure signal and motor current data was collected at P-8 for a heart pump system. This data is partially represented by points 310, 312, 314, 316, 318. Dashed lines 302, 304, 308 represent the linear scaling of the relationship between differential pressure and motor current. Specifically, line 302 represents linear scaling of the maximum differential pressure signal between P-levels. As the P-level increases, the maximum differential pressure signal increases. Line 304 represents linear scaling of the inflection point of the relationship between differential pressure and motor current between P-levels. As the P-level increases, the inflection point linearly increases. Line 308 represents linear scaling of the minimum differential pressure signal between P-levels. As the P-level increases, the minimum differential pressure signal decreases. For example, by determining the maximum differential pressure signal, minimum differential pressure signal and inflection point at P-8, the maximum differential pressure signal, minimum differential pressure signal, and inflection points may be calculated for P-1 through P-7 and P-9. In some implementations, the scaling between P-levels may be accomplished using a scaling factor. To determine the scaling factor, the maximum, minimum, and inflection points are found at all P-levels for a series of N heart pump systems. All N heart pump systems are the same kind of heart pump system, operating under similar conditions. Linear fits are calculated for the maximum, minimum, and inflection points across all P-levels for all the N heart pump systems data. These linear fits are then used to determine the scaling factor for the N heart pump system's maximum, minimum, and inflection points. The three scaling factors for the N pumps are very similar, and they are then averaged to determine a general scaling factor for all pump of that pump type.

As can be seen in each of curves P-1 through P-9, for a given motor current value, there may be multiple corresponding differential pressure signal values, even for a single performance level curve. The corresponding differential pressure signal values for a single motor current value are either categorized as "Phase A" or "Phase B". Plotted values of P-1 through P-9 that are above the inflection point line 304 are categorized as Phase B values. Plotted values of P-1 through P-9 that are below the inflection point line 304 are categorized as Phase A values. For example, points 310, 312, 314, 316, 318 are Phase A values of P-level P-8. When determining an estimate of time-varying differential pressure, as described above, the systems and methods described herein determine whether a motor current signal is in Phase A or Phase B, and determine the corresponding estimate of differential pressure signal value accordingly. For example, if the measured motor current was 600 mA while operating at P-level P-8, the corresponding differential pressure signal value would be 42 mmHg if the measured motor current is in Phase A and would be 110 mmHg is the measured motor current is in Phase B. Methods of distinguishing between Phase A and Phase B from measured motor current values will be described below in relation to FIGS. 6-7.

FIG. 4 shows plots of motor current, differential pressure signal, and flow over time, according to certain implementations. The y-axis of plot 410 indicates motor current measured in milliamps (mA), the y-axis of plot 420 indicates differential pressure signal measured in millimeters of mercury (mmHg), and the y-axis of plot 430 indicates flow in liters per minute (L/m). Plots 410, 420, 430 are representative of the same period of time, measured in samples along the respective x-axes of the plots. The plots vary in a somewhat cyclical manner, such that each plot has alternating peaks and troughs. A peak of motor current 410 corresponds to a trough in differential pressure signal 420 and a peak in flow 430. For example, at the 100 samples mark, the motor current 410 is at a local maximum, while the differential pressure signal 420 is at a local minimum at the same time.

Plots 410 and 420 represent data measured from current and pressure sensors, respectively, for a single heart pump system, such as that described above in relation to FIG. 1. Each "dot" along the plots represents a measured data point. The measured data points were best-fit to provide the plots 410 and 420. The data represented by plots 410 and 420 is used as training data, as described above to build a model representative of the relationship between differential pressure and motor current relationship for the heart pump system.

FIG. 5 shows a plot of differential pressure signal versus motor current for a specific heart pump system, according to certain implementations. The y-axis of plot 500 represents differential pressure signal in mmHg, while the x-axis represents motor current in mA. At a specific point in time, differential pressure signal and motor current are measured for a particular heart pump. These two measurements are notated by a dot in plot 500. For example, the data points from plots 410 and 420 of FIG. 4, described above, may be represented by dots in plot 500. A multilinear approximation may be used to determine a best-fit curve 510 to represent the training data. Best-fit curve 510 is representative of the specific heart pump system used in this instance to acquire the data shown in FIGS. 4 and 5.

From plots depicting motor current over time, such as FIGS. 6 and 7, the systems and methods described herein may determine if a heart pump system is in Phase A or Phase B. The slope of a direct line between the start point and end point of diastole indicates whether the system is in Phase A or Phase B. A positive slope is indicative of Phase A, while a negative slope is indicative of Phase B. A local motor current minimum occurs directly before systole in Phase B, while a local motor current minimum occurs directly after systole in Phase A. Whether a heart pump system is in Phase A or Phase B depends on patient pressure and P-level. Phase B is more likely to occur at lower P-levels (and lower motor current values). Higher differential pressure signal values occur in Phase B.

FIG. 6 shows a plot of motor current over time for Phase A, according to certain implementations. The y-axis of plot 600 represents motor current in mA, while the x-axis represents time in samples. Circle 602 indicates the start of diastole. Circle 604 indicates the end of diastole. The slope between circles 602 and 604 is positive, indicating that the heart pump system is in Phase A.

FIG. 7 shows a plot of motor current over time for Phase B, according to certain implementations. The y-axis of plot 700 represents motor current in mA, while the x-axis represents time in samples. Circle 702 indicates the start of diastole. Circle 704 indicates the end of diastole. The slope between circles 602 and 604 is negative, indicating that the heart pump system is in Phase B.

FIG. 8 shows a plot of differential pressure signal versus motor current for a heart pump system, according to certain implementations. The y-axis of plot 800 represents differential pressure signal in mmHg, while the x-axis represents motor current in mA. Line 810 demarcates a motor current value of 710 mA. Inflection point 840, at approximately 50 mmHg, indicates the "change" from Phase A to Phase B. Points above inflection point 840 are in Phase B, while points below inflection point 840 are in Phase A. At higher motor current values (over approximately 730 mA), the heart pump system operates in Phase A and there are no longer corresponding Phase B values. Circles 820 and 830 indicate two potential differential pressure signal values corresponding to the 710 mA motor current value indicated by line 810. Circle 820 indicates a value of approximately 40 mmHg, and is in Phase A. Circle 830 indicates the corresponding Phase B value of approximately 90 mmHg.

FIG. 9 shows a plot over time of real, simulated and simulated Phase A differential pressure signals, according to certain implementations. The y-axis of plot 900 represents differential pressure signal in mmHg, while the x-axis represents time in samples. Curve 910 shows the differential pressure signal as measured by a differential pressure sensor of a heart pump system. The simulated differential pressure signal curve is an estimated differential pressure signal, as simulated by the systems and methods described herein and overlaps entirely with curve 912. The simulated curve is therefore not visible in plot 900. Curve 912 is indicative of a "Phase A" differential pressure signal simulation according to the systems and methods described herein. The simulated Phase A differential pressure signal 912 and simulated differential pressure signal match entirely because the heart pump system operated entirely in Phase A during this time frame, as can be confirmed by the positive slope during diastolic phases. Plot 900 may be used to validate the performance of the simulated differential pressure signal. As can be seen in plot 900, the real differential pressure signal 910 and simulated differential pressure signal 912 match quite closely. The period, average, maximum, and minimum of the two signals 910 and 912 are especially close. These values are significant metrics used in flow, positioning and suction calculations. Differential pressure signal minimum is used to determine flow maximum; differential pressure signal maximum is used to determine flow minimum; and differential pressure signal average is used to determine flow average. Flow average, maximum, and minimum may be displayed to a clinician through a user interface.

FIG. 10 shows a plot of over time of real, simulated and simulated Phase A differential pressure signals, according to certain implementations. The y-axis of plot 1000 represents differential pressure signal in mmHg, while the x-axis represents time in samples. Curve 1010 shows the differential pressure signal as measured by a differential pressure sensor of a heart pump system. Curve 1012 shows an estimated differential pressure signal, as simulated by the systems and methods described herein. Curve 1014 partially overlaps with curve 1012 and is indicative of a "Phase A" differential pressure signal simulation according to the systems and methods described herein. The simulated Phase A differential pressure signal 1014 and simulated differential pressure signal 1012 do not match entirely (mostly deviated around the peaks) because the heart pump system operated at least partially in Phase B during this time frame, as can be confirmed by the negative slope during diastole cycles. Plot 1000 demonstrates the importance of determining whether the heart pump system is operating in Phase A or Phase B. While the simulated Phase A signal 1014 matched the period and minimum real values quite closely, it did not match the maximum or average values measured by the differential pressure sensor and shown in curve 1010. While simulated curve 1012 does not entirely overlap with real signal 1010, it provides a good enough estimation of the real differential pressure signal (especially the minimum and maximum values) by taking into account Phase B, which can be used for flow calculation and position/suction alarms.

FIG. 11 shows plots of differential pressure signal, motor current and rotations per minute (RPM) for a heart pump system over time, when the performance level of the heart pump system has changed, according to certain implementations. Plot 1110 shows differential pressure signal validation, plot 1120 shows motor current over time, and plot 1130 shows RPM over time. The three plots 1110, 1120, 1130 are indicative of simultaneous measurements of the same heart pump system operated over the same time period. The y-axis of plot 1110 represents differential pressure signal in mmHg, while the x-axis represents time in samples. Curve 1112 represents differential pressure signal measured by a differential pressure sensor. Curve 1114 represents an estimate of differential pressure signal. The y-axis of plot 1120 represents motor current in mA, while the x-axis represents time in samples. Curve 1122 represents motor current over time as measured by the heart pump system. The y-axis of plot 1130 represents RPM, while the x-axis represents time in samples. Curve 1132 represents RPM over time as measured by the heart pump system. Boxes 1116, 1126, 1136 denote a period of time of operation of the heart pump system at a first P-level. Boxes 1118, 1128, 1138 denote a period of time of operation of the heart pump system at a second P-level. The second P-level is lower than the first P-level. Once the P-level was lowered between boxes 1116, 1126, 1136 and boxes 1118, 1128, 1138, the RPM and motor current all decreased.

As represented by FIGS. 11-13, the heart pump system was run at the first P-level to acquire training data comprising motor current and differential pressure signal data. The training data was used to determine a relationship between the motor current and differential pressure signal data at that P-level. The relationship was then used to determine the estimate of differential pressure signal shown by curve 1114 in box 1116, which closely matched the measured differential pressure signal shown by curve 1112. The heart pump system was then operated at the second, lower P-level. The relationship between differential pressure and motor current was scaled to account for the lower P-level, as described above in relation to FIG. 3. The estimated differential pressure signal was then determined at this second P-level using the scaled, determined relationship. The estimated differential pressure signal 1114 again closely matched the measured differential pressure signal 1112, as shown in box 1118.

FIG. 12 shows plots of differential pressure signal and motor current over time at a first P-level, according to certain implementations. Plot 1210 is an enlarged view of box 1116 as shown in FIG. 11. The y-axis of plot 1210 shows differential pressure signal measured in mmHg. Plot 1220 is an enlarged view of box 1126 as shown in FIG. 11. The y-axis of plot 1220 shows motor current measured in mA. The x-axes of plots 1210 and 1220 show time measured in samples for the same time period. Plot 1210 displays measured differential pressure signal curve 1212, simulated placement curve 1214, and simulated Phase A differential pressure signal curve 1216. Simulated Phase A differential pressure signal curve 1212 almost overlaps simulated differential pressure signal curve 1214, indicating the differential pressure estimation was accurate.

FIG. 13 shows plots of differential pressure signal and motor current over time at a second P-level, according to certain implementations. Plot 1310 is an enlarged view of box 1118 as shown in FIG. 11. The y-axis of plot 1310 shows differential pressure signal measured in mmHg. Plot 1320 is an enlarged view of box 1128 as shown in FIG. 11. The y-axis of plot 1220 shows motor current measured in mA. The x-axes of plots 1310 and 1320 show time measured in samples for the same time period. Plot 1310 displays measured differential pressure signal curve 1312, simulated placement curve 1314, and simulated Phase A differential pressure signal curve 1316. Simulated Phase A differential pressure signal curve 1312 almost overlaps simulated differential pressure signal curve 1314, indicating the differential pressure estimation was accurate.

Even though the relationship between differential pressure and motor current had not been "built" using training data acquired at the second P-level, the estimated differential pressure signal 1314 still closely matched the measured differential pressure signal 1312 at that P-level. These results indicate that the scaling process used when switching between P-levels is reliable and provides results on par with those measured at the P-level used for training.

Figure 14:
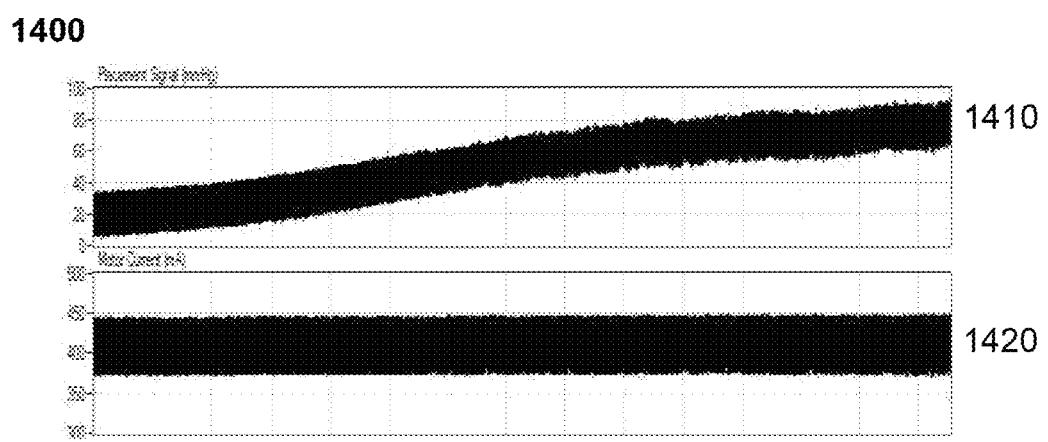
FIG. 14 shows plots of differential pressure signal drift and motor current over time, according to certain implementations.

FIG. 14 shows plots of differential pressure signal drift and motor current over time, according to certain implementations. The y-axis of plot 1410 represents differential pressure signal in mmHg, while the x-axis represents time in samples. The y-axis of plot 1420 represents motor current in mA, while the x-axis represents time in samples over the same time period as that represented in plot 1410. Motor current 1420 is maintained over time, with roughly the same mean value for the entire time period. During this same time period, the differential pressure signal (as measured by a pressure sensor) increased significantly, from a mean value of approximately 20 mmHg to a mean value of approximately 80 mmHg. When the mean motor current value is steady over a significant period of time, the mean differential pressure signal should also be steady for that period of time. Differential pressure signal 1410 is "drifting" in this case, indicating that the pressure sensor is no longer providing an accurate measurement.

Figure 15:
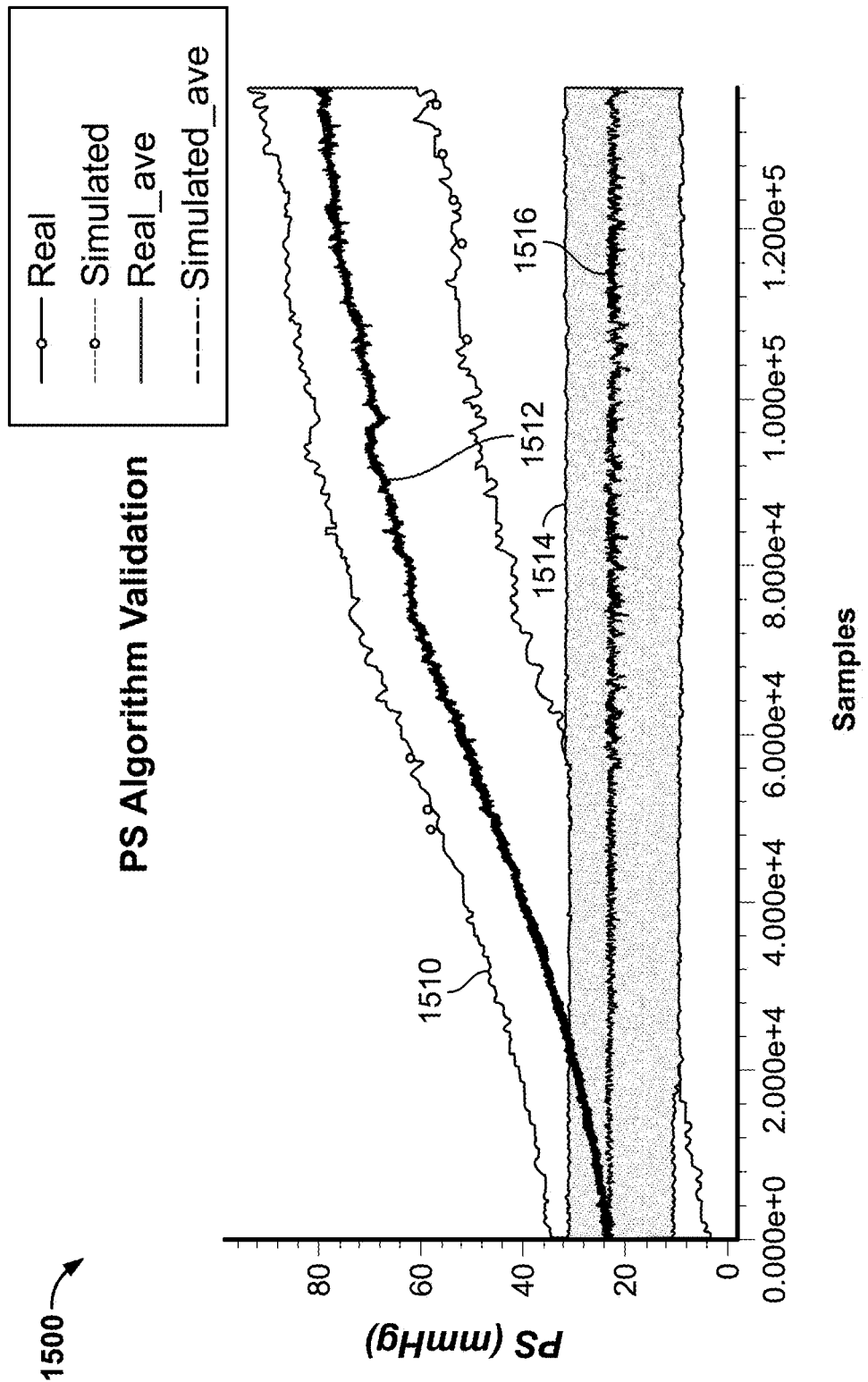
FIG. 15 shows plots of differential pressure signal drift and estimated differential pressure signal over a period of time, according to certain implementations.

FIG. 15 shows plots of differential pressure signal drift and estimated differential pressure signal over time, according to certain implementations. The y-axis of plot 1500 represents differential pressure signal in mmHg, while the x-axis represents time in samples. Curve 1510 represents measured differential pressure signal, curve 1512 represents the average of the measured differential pressure signal, curve 1514 represents simulated differential pressure signal, and curve 1516 represents the average of the simulated differential pressure signal. Measured differential pressure signal 1510 is drifting, while the estimate of the differential pressure signal (the simulated differential pressure signal) 1514 remains steady. If the measured differential pressure signal diverges from the simulated differential pressure signal, particularly after a period of time where the average measured differential pressure signal 1512 closely matched the simulated average differential pressure signal 1516, the systems and methods described herein may determine the pressure sensor (providing the measured differential pressure signal data) needs to be recalibrated. In some implementations, the sensor may be re-calibrated automatically. In some aspects, the heart pump system may display a notification to the user indicating the sensor needs to be re-calibrated.

In some implementations, to determine whether the differential pressure signal is drifting, the systems and methods described herein may calculate a difference between the differential pressure signal or the average of the differential pressure signal (e.g., curve 1512) and the estimate of the differential pressure signal (e.g., curve 1516) or the average of the estimate. This difference may be compared to a threshold. If the difference exceeds the threshold, the differential pressure signal had drifted. If the difference is below the threshold, the differential pressure signal has not drifted. The threshold may be 10 mmHg, 20 mmHg, or any suitable amount. For example, the threshold may be 15 mmHg, and the curve 1512 may be determined to be drifting at sample 4.000e+4 in FIG. 15. In some implementations, the system may determine a first difference between the measured differential pressure signal and the estimate at a first time and a second difference between the measured differential pressure signal and the estimate at a second time. If the second difference is substantially larger than the first difference, the system may determine the measured pressure signal has drifted. In some implementations, the difference between the measured differential pressure signal and the estimate may be measured periodically or continuously monitored. If the difference increases over time, the system may determine the measured pressure signal is drifting.

FIGS. 16-18 show metrics for measuring the success of flow estimation based on simulated differential pressure signal, such as the simulated differential pressure signal from the systems and methods described above, according to certain implementations. FIGS. 16-18 result from a validation test performed using data from pumps with reliable differential pressure signals (e.g., pumps containing accurate differential pressure sensors that did not fail during testing). Flow is an important metric for a clinician's use in determining how the pump is doing. To understand the performance and status of the heart pump system, the clinician may require the mean, maximum, and minimum flow values, which may be displayed to the clinician through a user interface.

FIG. 16 shows a histogram of mean flow estimation error, according to certain implementations. Display 1600 comprises a mean flow estimation histogram, an estimation error distribution, a confidence interval distribution, and a results table. The mean flow estimation error histogram is centered at zero with a narrow peak, indicating matching results, with little error. The mean flow estimation error is representative of the difference between the mean of the flow calculated from the measured differential pressure signal and the mean of the flow calculated from estimate of differential pressure signal.

FIG. 17 shows a histogram of maximum flow estimation error, according to certain implementations. Display 1700 comprises a maximum flow estimation error bar graph, an estimation error distribution, a confidence interval distribution, and a results table. The maximum flow estimation error histogram is centered at zero with a narrow peak, indicating matching results, with little error. The maximum flow estimation error is representative of the difference between the local maximums of the flow calculated from the measured differential pressure signal and the local maximums of flow calculated from the estimate of differential pressure signal.

FIG. 18 shows a histogram of minimum flow estimation error, according to certain implementations. Display 1800 comprises a minimum flow estimation error bar graph, an estimation error distribution, a confidence interval distribution, and a results table. The minimum flow estimation error histogram is centered at zero with a narrow peak, indicating matching results, with little error. The minimum flow estimation error is representative of the difference between the local minimums of the flow calculated from the measured differential pressure signal and the local minimums of the flow calculated from the estimate of differential pressure signal.

In some aspects, the heart pump system may output suction and/or position alarms. The reliability of such alarms when relying on an estimated rather than measured differential pressure signal may be a useful metric for determining the efficacy of the estimated differential pressure signal. In some implementations, a position alarm may be triggered if the pulsatility of the differential pressure signal is less than a threshold value. The alarm may indicate that the positioning of the heart pump system within a patient's heart is incorrect. For example, the position alarm may be triggered if the pulsatility of the differential pressure signal falls below 10 mmHg. This alarm may prompt a clinician to adjust the positioning of the heart pump system. If the pressure sensor measuring the differential pressure signal fails, the heart pump system may rely on the estimated differential pressure signal (determined by the systems and methods described above) to trigger the position alarm. To determine the reliability of the estimated differential pressure signal in triggering the position alarm, real alarm cases triggered by measured differential pressure signal values were compared to estimated differential pressure signals triggering alarms for the same cases. A differential pressure signal error allowance may be built in to the alarm calculation in order to more reliably trigger the alarm. This allowance is built into the testing environment in this case to address the cases for leading to false positive or false negative alarm when the cases are barely above or barely below the threshold. As shown in Table 1, the total position alarm precision for the estimated differential pressure signal for 20 cases was 97.9%, while the position alarm recall was 100.0%.

In some aspects, a suction alarm may be triggered if the differential pressure signal is greater than a threshold for a period of time. The suction alarm may only be triggered if the heart pump system is operating in certain P-levels. For example, the suction alarm may be triggered if the differential pressure signal is greater than a threshold for 10% of the 3 seconds window when operating in one of P-levels P5-P9. A suction error allowance may be built in to the alarm calculation in order to more reliably trigger the alarm. This allowance is built into the testing environment in this case to address the cases for leading to false positive or false negative alarm when the cases are barely above or barely below the threshold. As shown in Table 1, the total suction alarm precision for the estimated differential pressure signal for 30 cases was 80.6%, while the position alarm recall was 93.2%.

TABLE 1

| Position Alarm Precision | Position Alarm Recall |
|---|---|
| 97.9% | 100.0% |
| Suction Alarm Precision | Suction Alarm Recall |
| 80.6% | 93.2% |

The foregoing is merely illustrative of the principles of the disclosure, and the apparatuses can be practiced by other than the described aspects, which are presented for purposes of illustration and not of limitation. It is to be understood that the apparatuses disclosed herein, while shown for use in percutaneous insertion of heart pumps, may be applied to apparatuses in other applications requiring hemostasis.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

The systems and methods described may be implemented locally on a heart pump system or a controller of a heart pump system, such as the AIC. The heart pump system may comprise a data processing apparatus. The systems and methods described herein may be implemented remotely on a separate data processing apparatus. The separate data processing apparatus may be connected directly or indirectly to the heart pump system through cloud applications. The heart pump system may communicate with the separate data processing apparatus in real-time (or near real-time).

In general, aspects of the subject matter and the functional operations described in this specification can be implemented in digital electronic circuitry, or in computer software, firmware, or hardware, including the structures disclosed in this specification and their structural equivalents, or in combinations of one or more of them. Aspects of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter affecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program may correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

Examples of changes, substitutions, and alterations are ascertainable by one skilled in the art and could be made without departing from the scope of the information disclosed herein. All references cited herein are incorporated by reference in their entirety and made part of this application.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A heart pump system comprising:
   a pump comprising a pump housing and a rotor, the pump housing having a proximal end and a distal end;
   a cannula comprising a proximal end that interfaces with the distal end of the pump housing and a distal end, the pump being configured to be operated by a motor;
   an elongate catheter extending proximal of the pump housing;
   a differential pressure sensor; and
   a controller configured to:
      receive first data indicative of a time-varying motor current during a first period of time, wherein the time-varying motor current corresponds to an amount of current delivered to the motor while the heart pump system is operating in a patient,
      receive second data from the differential pressure sensor, wherein the second data is indicative of a time-varying differential pressure during the first period of time,
      receive third data indicative of time-varying motor current during a second period of time later than the first period of time,
      determine an estimate of time-varying differential pressure during the second period of time from the third data and a relationship between the first data and the second data,
      receive fourth data from the differential pressure sensor, the fourth data indicative of the time-varying differential pressure during the second period of time, determine the time-varying differential pressure indicated by the fourth data is drifting based on a comparison of (a) the time-varying differential pressure during the second period of time indicated by the fourth data, to (b) the estimate of time-varying differential pressure during the second period of time, and in response to determining the time-varying differential pressure during the second period of time is drifting, automatically re-calibrating the differential pressure sensor.

2. The heart pump system of claim 1, wherein the controller is configured to determine the estimate of time-varying differential pressure during the second period of time in response to determining that the differential pressure sensor has failed.

3. The heart pump system of claim 2, wherein the controller is further configured to:
provide a first indicator that the differential pressure sensor has failed; and
provide a second indicator that the estimate of time-varying differential pressure during the second period of time is simulated.

4. The heart pump system of claim 1, wherein the determining that the differential pressure sensor has failed occurs when no data is received from the differential pressure sensor during the second period of time.

5. The heart pump system of claim 1, wherein the controller is further configured to determine the estimate of time-varying differential pressure during the second period of time based on determining a time series of estimated points by determining whether the third data corresponds to a first phase or a second phase in the relationship between the first data and the second data.

6. The heart pump system of claim 5, wherein the controller is further configured to identify whether the third data corresponds to the first phase or the second phase by:
determining a diastolic period within the third data, wherein the diastolic period starts at a starting point and ends at an ending point in time;
determining a slope of the third data between the starting point and the ending point;
in response to determining the slope is positive, determining the third data corresponds to the first phase; and
in response to determining the slope is negative, determining the third data corresponds to the second phase.

7. The heart pump system of claim 1, wherein the controller is further configured to:
determine, based on the estimate of time-varying differential pressure, at least one of: flow rate, position, and suction associated with the heart pump system.

8. The heart pump system of claim 1, wherein the controller is further configured to display at least one of: the time-varying differential pressure, the motor current, and the estimate of time-varying differential pressure.

9. The heart pump system of claim 1, wherein the controller is further configured to determine the time-varying differential pressure is drifting by:
calculating, based on the comparison of (a) to (b), a difference between the time-varying differential pressure indicated by the fourth data and the estimate of time-varying differential pressure over the second period of time,
comparing the difference to a differential pressure signal threshold, and determining, based on comparing the difference to the differential pressure signal threshold, the difference is greater than the differential pressure signal threshold.

10. The heart pump system of claim 9, wherein the differential pressure signal threshold is at least 10 mmHg.

11. The heart pump system of claim 1, wherein the controller is further configured to:
based on determining that the time-varying differential pressure is drifting during the second period of time, display a notice indicating the differential pressure sensor needs to be re-calibrated.

12. The heart pump system of claim 1, wherein the time-varying differential pressure corresponds to a difference in pressure between an inner portion of the heart pump system and an outside of the heart pump system.

13. The heart pump system of claim 1, wherein the controller is configured to determine the relationship between the first data and the second data by:
determining a correlation, for each point of time in the first period of time, between the motor current and the time-varying differential pressure, and
calculating a multilinear fit for correlation, wherein the multilinear fit is indicative of operating characteristics of the heart pump system.

14. The heart pump system of claim 1, wherein the first data and second data are representative of the heart pump system operating at a first operating level, and wherein the controller is further configured to:
change operation of the heart pump system to a second operating level, and
scale, based on changing the operation of the heart pump system to the second operating level, the relationship between the first and second data to account for the second operating level,
wherein the controller is configured to determine the estimate of time-varying differential pressure based on the scaled relationship.

15. The heart pump system of claim 1, wherein the pump is configured to be placed such that the cannula extends across an aortic valve of the patient, the distal end being located within a left ventricle of the patient, and the proximal end being located within an aorta of the patient.

16. The heart pump system of claim 1, further comprising a flexible projection extending distally away from the distal end of the cannula.

17. The heart pump system of claim 1, wherein the elongate catheter is coupled on its distal end to the pump housing and wherein the pump further comprises a drive cable extending through the elongate catheter.

18. A controller configured to:
receive first data indicative of a time-varying motor current during a first period of time, wherein the time-varying motor current corresponds to an amount of current delivered to a motor of a heart pump system, while the heart pump system is operating in a patient;
receive second data from a differential pressure sensor of the heart pump system, wherein the second data is indicative of a time-varying differential pressure during the first period of time;
receive third data indicative of time-varying motor current during a second period of time later than the first period of time;
determine an estimate of time-varying differential pressure during the second period of time from the third data and a relationship between the first data and the second data;

receive fourth data from the differential pressure sensor, the fourth data indicative of the time-varying differential pressure during the second period of time;

determine the time-varying differential pressure indicated by the fourth data is drifting based on a comparison of (a) the time-varying differential pressure during the second period of time indicated by the fourth data, to (b) the estimate of time-varying differential pressure during the second period of time; and in response to determining the time-varying differential pressure during the second period of time is drifting, automatically re-calibrating the differential pressure sensor.

19. A method for automatically re-calibrating a differential pressure sensor of a heart pump system, the method comprising:

receiving, by a controller, first data indicative of a time-varying motor current during a first period of time, wherein the time-varying motor current corresponds to an amount of current delivered to a motor of the heart pump system, while the heart pump system is operating in a patient;

receiving, by the controller, second data from a differential pressure sensor of the heart pump system, wherein the second data is indicative of a time-varying differential pressure during the first period of time;

receiving, by the controller, third data indicative of time-varying motor current during a second period of time later than the first period of time;

determining, by the controller, an estimate of time-varying differential pressure during the second period of time from the third data and a relationship between the first data and the second data;

receiving, by the controller, fourth data from the differential pressure sensor, the fourth data indicative of the time-varying differential pressure during the second period of time;

determining, by the controller, the time-varying differential pressure indicated by the fourth data is drifting based on a comparison of (a) the time-varying differential pressure during the second period of time indicated by the fourth data to (b) the estimate of time-varying differential pressure during the second period of time; and in response to determining the time-varying differential pressure during the second period of time is drifting, automatically re-calibrating, by the controller, the differential pressure sensor.

* * * * *